US010589120B1

(12) United States Patent
Bellinger

(10) Patent No.: US 10,589,120 B1
(45) Date of Patent: Mar. 17, 2020

(54) HIGH-INTENSITY LASER THERAPY METHOD AND APPARATUS

(71) Applicant: Gary John Bellinger, Dallas, TX (US)

(72) Inventor: Gary John Bellinger, Dallas, TX (US)

(\*) Notice: Subject to any disclaimer, the term of this patent is extended or adjusted under 35 U.S.C. 154(b) by 0 days.

(21) Appl. No.: 15/967,121

(22) Filed: Apr. 30, 2018

Related U.S. Application Data

(63) Continuation-in-part of application No. 15/157,320, filed on May 17, 2016, which is a continuation-in-part of application No. 14/145,356, filed on Dec. 31, 2013, now abandoned, application No. 15/967,121, filed on Apr. 30, 2018, which is a continuation of application No. 14/789,958, filed on Jul. 1, 2015, now abandoned.

(60) Provisional application No. 61/747,745, filed on Dec. 31, 2012, provisional application No. 62/019,702, filed on Jul. 1, 2014, provisional application No. 62/019,708, filed on Jul. 1, 2014.

(51) Int. Cl.
*A61N 5/00* (2006.01)
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0659* (2013.01)

(58) Field of Classification Search
None
See application file for complete search history.

(56) References Cited

U.S. PATENT DOCUMENTS

| 4,634,557 A | 1/1987 | Sato |
| 4,686,979 A | 8/1987 | Gruen et al. |
| 4,930,504 A | 6/1990 | Diamantopoulos et al. |
| 4,995,691 A | 2/1991 | Purcell, Jr. |

(Continued)

FOREIGN PATENT DOCUMENTS

| DE | 69827286 T2 | 12/2004 |
| EP | 1021223 B1 | 10/2004 |

(Continued)

OTHER PUBLICATIONS

Gordts et al, The Impact of Lipoproteins on Wound Healing: Topical HDL Therapy Corrects Delayed Wound Healing in Apolipoprotein E Deficient Mice, Pharmaceuticals (Basel). Apr. 2014; 7(4): 419-432 (Year: 2014).*

(Continued)

*Primary Examiner* — Michael W Kahelin
*Assistant Examiner* — Sana Sahand
(74) *Attorney, Agent, or Firm* — Law Office of Sam Sokhansanj PLLC

(57) ABSTRACT

A method of laser irradiation for alleviating the physical symptoms associated with acute or chronic inflammatory conditions, which can include directing a laser beam from a laser unit in a continuous wave operation having a wavelength of approximately 1275 nm and a power output level in the range of from one (1) Watt up to and including 75 Watts on an inflamed area that is to be treated, such that the laser beam penetrates the inflamed area in the range of from 0.1 cm to 30 cm. In addition, the laser beam from the laser unit can be configured to activate intracellular photoreceptors, thereby initiating a cascade of secondary cellular metabolic effects and normalizing cellular activity towards homeostasis.

17 Claims, 18 Drawing Sheets

(56) References Cited

U.S. PATENT DOCUMENTS

| | | | |
|---|---|---|---|
| 5,062,431 A | 11/1991 | Potter | |
| 5,071,416 A | 12/1991 | Heller et al. | |
| 5,259,380 A | 11/1993 | Mendes et al. | |
| 5,290,272 A | 3/1994 | Burstein et al. | |
| 5,358,503 A | 10/1994 | Bertwell et al. | |
| 5,445,146 A * | 8/1995 | Bellinger | A01M 1/02 606/3 |
| 5,464,436 A | 11/1995 | Smith | |
| 5,496,306 A | 3/1996 | Engelhardt et al. | |
| 5,496,307 A | 3/1996 | Daikuzono | |
| 5,514,127 A | 5/1996 | Shanks | |
| 5,599,340 A | 2/1997 | Simon et al. | |
| 5,616,140 A | 4/1997 | Prescott | |
| 5,755,752 A | 5/1998 | Segal | |
| 5,846,252 A | 12/1998 | Mehl, Sr. | |
| 5,871,479 A | 2/1999 | Furumoto et al. | |
| 5,951,596 A * | 9/1999 | Bellinger | A01M 1/02 606/9 |
| 5,971,978 A | 10/1999 | Mukai | |
| 6,045,548 A | 4/2000 | Furumoto et al. | |
| 6,061,591 A | 5/2000 | Freitag et al. | |
| 6,084,242 A | 7/2000 | Brown, Jr. et al. | |
| 6,090,101 A | 7/2000 | Duon et al. | |
| 6,099,520 A | 8/2000 | Shimoji | |
| 6,099,554 A | 8/2000 | Nordquist et al. | |
| 6,110,165 A | 8/2000 | Ota | |
| 6,156,028 A | 12/2000 | Prescott | |
| 6,165,205 A | 12/2000 | Neuberger | |
| 6,214,033 B1 | 4/2001 | Ii et al. | |
| 6,238,426 B1 | 5/2001 | Chen | |
| 6,267,779 B1 * | 7/2001 | Gerdes | A61N 5/0616 606/3 |
| 6,290,714 B1 | 9/2001 | Streeter | |
| 6,302,878 B1 | 10/2001 | Daikuzono | |
| 6,306,160 B1 | 10/2001 | Nidetzlcy | |
| 6,312,451 B1 | 11/2001 | Streeter | |
| 6,319,274 B1 | 11/2001 | Shadduck | |
| 6,383,175 B1 | 5/2002 | Ii et al. | |
| 6,409,744 B1 * | 6/2002 | Marchesi | A61F 7/00 606/13 |
| 6,413,267 B1 | 7/2002 | Dumoulin-White et al. | |
| 6,454,791 B1 | 9/2002 | Prescott | |
| 6,503,268 B1 | 1/2003 | Neuberger et al. | |
| 6,527,797 B1 | 3/2003 | Masotti et al. | |
| 6,530,921 B1 | 3/2003 | Maki | |
| 6,569,156 B1 | 5/2003 | Tankovich et al. | |
| 6,582,421 B1 | 6/2003 | Mordon et al. | |
| 6,582,454 B2 | 6/2003 | Yayama | |
| 6,605,080 B1 | 8/2003 | Altshuler et al. | |
| 6,613,040 B2 | 9/2003 | Tankovich et al. | |
| 6,632,218 B1 | 10/2003 | Furumoto et al. | |
| 6,652,512 B2 | 11/2003 | Ota | |
| 6,673,095 B2 | 1/2004 | Nordquist | |
| 6,679,837 B2 | 1/2004 | Daikuzono | |
| 6,692,517 B2 | 2/2004 | Cho et al. | |
| 6,808,523 B2 | 10/2004 | Fujisaka et al. | |
| 6,811,563 B2 | 11/2004 | Savage, Jr. et al. | |
| 6,858,009 B2 | 2/2005 | Kawata et al. | |
| 6,913,616 B2 | 7/2005 | Hamilton et al. | |
| 6,936,043 B2 | 8/2005 | Peyman | |
| 6,942,655 B2 | 9/2005 | Peyman | |
| 6,997,923 B2 | 2/2006 | Anderson et al. | |
| 7,016,718 B2 | 3/2006 | Ii et al. | |
| 7,018,395 B2 | 3/2006 | Chen | |
| 7,060,061 B2 | 6/2006 | Altshuler et al. | |
| 7,066,941 B2 | 6/2006 | Perricone | |
| 7,204,846 B2 | 4/2007 | Suzuki | |
| 7,232,456 B2 | 6/2007 | Chernoff | |
| 7,264,629 B2 | 9/2007 | Simkin et al. | |
| 7,322,972 B2 | 1/2008 | Viator et al. | |
| 7,331,964 B2 | 2/2008 | Maricle et al. | |
| 7,344,555 B2 | 3/2008 | Anders et al. | |
| 7,392,077 B2 | 6/2008 | Mueller et al. | |
| 7,402,167 B2 | 7/2008 | Nemenov | |
| 7,458,983 B2 | 12/2008 | Hamilton et al. | |
| 7,695,504 B2 | 4/2010 | Anders et al. | |
| 7,771,417 B2 | 8/2010 | Telfair et al. | |
| 7,794,453 B2 | 9/2010 | Zemmouri et al. | |
| 7,840,263 B2 | 11/2010 | Girouard et al. | |
| 7,846,151 B2 | 12/2010 | Hayashi et al. | |
| 7,887,533 B2 | 2/2011 | Barolet et al. | |
| 7,912,108 B2 | 3/2011 | Tao et al. | |
| 7,914,523 B2 | 3/2011 | Barolet et al. | |
| 8,025,687 B2 | 9/2011 | Streeter et al. | |
| 8,029,553 B2 | 10/2011 | Nemenov | |
| 8,033,284 B2 | 10/2011 | Porter et al. | |
| 8,066,696 B2 | 11/2011 | Abe | |
| 8,105,321 B2 | 1/2012 | Zemmouri et al. | |
| 8,136,531 B2 | 3/2012 | Chariff | |
| 8,149,526 B2 | 4/2012 | DeLapp et al. | |
| 8,167,921 B2 | 5/2012 | Streeter et al. | |
| 8,251,983 B2 | 8/2012 | Larson et al. | |
| 8,252,033 B2 | 8/2012 | Tucker et al. | |
| 8,308,784 B2 | 11/2012 | Streeter et al. | |
| 8,316,850 B2 | 11/2012 | Porter et al. | |
| 8,316,860 B1 | 11/2012 | Porter et al. | |
| 8,317,847 B2 | 11/2012 | Hosokawa et al. | |
| 8,328,795 B2 | 12/2012 | Domankevitz et al. | |
| 8,409,264 B2 | 4/2013 | Shanks et al. | |
| 8,430,104 B2 | 4/2013 | Hennings et al. | |
| 8,480,719 B2 | 7/2013 | Fortuna et al. | |
| 8,483,819 B2 | 7/2013 | Choi et al. | |
| 8,518,094 B2 | 8/2013 | Wang | |
| 8,551,148 B2 | 10/2013 | Asakawa et al. | |
| 8,579,952 B2 | 11/2013 | Sun et al. | |
| 8,623,063 B2 | 1/2014 | Chung | |
| 8,701,675 B1 | 4/2014 | Schenker et al. | |
| 8,790,382 B2 | 7/2014 | Gerlitz | |
| 8,795,264 B2 | 8/2014 | Zipper | |
| 8,814,924 B2 | 8/2014 | Shanks et al. | |
| 8,932,278 B2 | 1/2015 | Tankovich et al. | |
| 8,945,196 B2 | 2/2015 | Huttemann et al. | |
| 9,017,391 B2 | 4/2015 | McDaniel | |
| 9,033,963 B2 | 5/2015 | Vera et al. | |
| 2001/0007079 A1 | 7/2001 | Chernoff | |
| 2002/0002367 A1 | 1/2002 | Tankovich et al. | |
| 2002/0004673 A1 | 1/2002 | Cho et al. | |
| 2002/0165525 A1 | 11/2002 | Nakamura | |
| 2003/0023283 A1 | 1/2003 | McDaniel | |
| 2003/0036785 A1 | 2/2003 | Ii et al. | |
| 2003/0093064 A1 | 5/2003 | Peyman | |
| 2003/0093065 A1 | 5/2003 | Peyman | |
| 2003/0109907 A1 | 6/2003 | Shadduck | |
| 2003/0111084 A1 | 6/2003 | Revazova et al. | |
| 2003/0114902 A1 | 6/2003 | Prescott | |
| 2003/0120325 A1 | 6/2003 | Fujisaka et al. | |
| 2003/0125783 A1 * | 7/2003 | Moran | A61N 5/0616 607/89 |
| 2003/0181962 A1 | 9/2003 | Streeter | |
| 2003/0199859 A1 | 10/2003 | Altshuler et al. | |
| 2004/0010300 A1 | 1/2004 | Masotti et al. | |
| 2004/0030369 A1 | 2/2004 | Kubota | |
| 2004/0039379 A1 | 2/2004 | Viator et al. | |
| 2004/0049248 A1 | 3/2004 | Schonborn | |
| 2004/0054386 A1 | 3/2004 | Martin et al. | |
| 2004/0111132 A1 * | 6/2004 | Shenderova | A61N 5/0616 607/88 |
| 2004/0111135 A1 | 6/2004 | Kim | |
| 2004/0162597 A1 | 8/2004 | Hamilton et al. | |
| 2005/0234383 A1 | 10/2005 | Dougal | |
| 2005/0234531 A1 | 10/2005 | Peyman | |
| 2005/0245998 A1 | 11/2005 | Pruitt et al. | |
| 2005/0256553 A1 | 11/2005 | Strisower | |
| 2006/0009823 A1 | 1/2006 | Richardson et al. | |
| 2006/0015158 A1 | 1/2006 | Hamilton et al. | |
| 2006/0036299 A1 | 2/2006 | Anders et al. | |
| 2006/0095095 A1 | 5/2006 | Cao | |
| 2006/0095101 A1 | 5/2006 | Dees et al. | |
| 2006/0111698 A1 | 5/2006 | Kwon | |
| 2006/0178713 A1 | 8/2006 | Maricle et al. | |
| 2006/0212100 A1 | 9/2006 | Wu et al. | |
| 2006/0235371 A1 | 10/2006 | Wakamatsu et al. | |
| 2007/0060984 A1 | 3/2007 | Webb et al. | |
| 2007/0123844 A1 | 5/2007 | Henry | |

(56) References Cited

U.S. PATENT DOCUMENTS

| | | | |
|---|---|---|---|
| 2007/0142880 A1 | 6/2007 | Barnard et al. |
| 2007/0154465 A1 | 7/2007 | Kharazi et al. |
| 2007/0162093 A1 | 7/2007 | Porter et al. |
| 2007/0185552 A1 | 8/2007 | Masotti et al. |
| 2007/0244495 A1 | 10/2007 | Kwon |
| 2007/0260229 A1 | 11/2007 | Navarro et al. |
| 2007/0260297 A1 | 11/2007 | Chariff |
| 2008/0009922 A1 | 1/2008 | Bille |
| 2008/0058787 A1 | 3/2008 | Gertner |
| 2008/0172045 A1 | 7/2008 | Shanks et al. |
| 2008/0172105 A1 | 7/2008 | Lin et al. |
| 2008/0183250 A1 | 7/2008 | Tanojo et al. |
| 2008/0188838 A1 | 8/2008 | Abe |
| 2008/0215020 A1* | 9/2008 | Reeves ............ A61F 13/00068 604/305 |
| 2008/0215123 A1 | 9/2008 | Maricle et al. |
| 2008/0243110 A1 | 10/2008 | Kang et al. |
| 2008/0269732 A1 | 10/2008 | Pyun |
| 2008/0269847 A1 | 10/2008 | Nemenov |
| 2009/0012508 A1* | 1/2009 | Dougal ................ A61B 18/203 606/9 |
| 2009/0043296 A1 | 2/2009 | Foster |
| 2009/0054788 A1 | 2/2009 | Hauger et al. |
| 2009/0069872 A1 | 3/2009 | Fortuna et al. |
| 2009/0082759 A1 | 3/2009 | Pryor et al. |
| 2009/0088733 A1 | 4/2009 | Anderson et al. |
| 2009/0093868 A1 | 4/2009 | Kim et al. |
| 2009/0112195 A1 | 4/2009 | Zemmouri |
| 2009/0132012 A1 | 5/2009 | Shanks |
| 2009/0185264 A1 | 7/2009 | Cameron et al. |
| 2009/0210036 A1 | 8/2009 | Hamilton et al. |
| 2009/0216300 A1 | 8/2009 | Keltner et al. |
| 2009/0222069 A1 | 9/2009 | Petersen et al. |
| 2009/0227997 A1 | 9/2009 | Wang et al. |
| 2009/0248041 A1 | 10/2009 | Williams et al. |
| 2009/0254154 A1 | 10/2009 | De Taboada et al. |
| 2010/0004644 A1 | 1/2010 | Zipper |
| 2010/0004645 A1 | 1/2010 | Jeong et al. |
| 2010/0016931 A1* | 1/2010 | Shanks ............... A61N 5/0613 607/89 |
| 2010/0049180 A1 | 2/2010 | Wells et al. |
| 2010/0076419 A1 | 3/2010 | Chew et al. |
| 2010/0076529 A1 | 3/2010 | Tucker et al. |
| 2010/0152715 A1 | 6/2010 | Srinivasan |
| 2010/0168823 A1 | 7/2010 | Strisower |
| 2010/0249763 A1 | 9/2010 | Larson et al. |
| 2010/0280580 A1 | 11/2010 | Hosokawa et al. |
| 2010/0312054 A1 | 12/2010 | Beyar et al. |
| 2011/0004202 A1 | 1/2011 | Zipper |
| 2011/0004203 A1 | 1/2011 | Zipper |
| 2011/0015707 A1 | 1/2011 | Tucker et al. |
| 2011/0040358 A1 | 2/2011 | Bean et al. |
| 2011/0066213 A1 | 3/2011 | Huttermann et al. |
| 2011/0092966 A1 | 4/2011 | Guo et al. |
| 2011/0130749 A1 | 6/2011 | Arcus Villacampa |
| 2011/0152744 A1 | 6/2011 | Choi et al. |
| 2011/0152977 A1 | 6/2011 | Sueyoshi et al. |
| 2011/0160814 A2 | 6/2011 | Tucker et al. |
| 2011/0172746 A1* | 7/2011 | Porter ...................... A61N 5/01 607/89 |
| 2011/0196357 A1 | 8/2011 | Srinivasan |
| 2011/0208273 A1 | 8/2011 | Fortuna et al. |
| 2011/0251602 A1 | 10/2011 | Anderson et al. |
| 2011/0251659 A1 | 10/2011 | Prescott |
| 2011/0301581 A1 | 12/2011 | Thyzel |
| 2011/0306919 A1 | 12/2011 | Latina et al. |
| 2011/0306920 A1 | 12/2011 | Lin et al. |
| 2011/0313407 A1 | 12/2011 | Rafailov et al. |
| 2011/0313408 A1 | 12/2011 | Tankovich et al. |
| 2012/0029604 A1 | 2/2012 | Sun et al. |
| 2012/0041522 A1 | 2/2012 | Hwang et al. |
| 2012/0083691 A1 | 4/2012 | Bille |
| 2012/0089135 A1 | 4/2012 | Srinivasan |
| 2012/0095533 A1 | 4/2012 | Wang |
| 2012/0143176 A1 | 6/2012 | Ryan et al. |
| 2012/0165799 A1 | 6/2012 | Yamamoto |
| 2012/0172851 A1 | 7/2012 | Lee et al. |
| 2012/0179227 A1 | 7/2012 | Schomacker et al. |
| 2012/0197358 A1 | 8/2012 | Prescott |
| 2012/0197359 A1 | 8/2012 | Tucker et al. |
| 2012/0220991 A1 | 8/2012 | Jenny et al. |
| 2012/0239059 A1 | 9/2012 | Jagger |
| 2012/0259321 A1 | 10/2012 | Vera et al. |
| 2012/0265274 A1 | 10/2012 | Gomez De Diego |
| 2012/0290047 A1 | 11/2012 | Hendy et al. |
| 2012/0303100 A1 | 11/2012 | Pryor et al. |
| 2012/0323230 A1 | 12/2012 | Larson et al. |
| 2012/0330291 A1 | 12/2012 | Jester et al. |
| 2013/0013029 A1 | 1/2013 | Chung |
| 2013/0035684 A1 | 2/2013 | Neuberger |
| 2013/0046363 A1 | 2/2013 | Thomas |
| 2013/0085557 A1 | 4/2013 | Terasawa |
| 2013/0103008 A1 | 4/2013 | Sramek |
| 2013/0172960 A1 | 7/2013 | Ahn et al. |
| 2013/0204235 A1 | 8/2013 | Palanker |
| 2013/0226157 A1 | 8/2013 | Huang |
| 2013/0253411 A1 | 9/2013 | Rubinchik et al. |
| 2013/0267855 A1 | 10/2013 | Tsubota et al. |
| 2013/0304164 A1 | 11/2013 | Zanata et al. |
| 2014/0088487 A1 | 3/2014 | Harris et al. |
| 2014/0135715 A1 | 5/2014 | Lambert et al. |
| 2014/0188094 A1 | 7/2014 | Islam |
| 2014/0296945 A1 | 10/2014 | Kato |
| 2014/0379053 A1 | 12/2014 | Boo et al. |
| 2015/0182755 A1 | 7/2015 | Bellinger |
| 2016/0296764 A1* | 10/2016 | Bellinger ............ A61N 5/0616 |

FOREIGN PATENT DOCUMENTS

| | | |
|---|---|---|
| WO | WO1997019725 A1 | 6/1997 |
| WO | WO9830283 A1 | 7/1998 |
| WO | WO1999019024 A1 | 4/1999 |
| WO | WO2000035534 A1 | 6/2000 |
| WO | WO2009088550 A2 | 7/2009 |
| WO | WO2010031777 A2 | 3/2010 |
| WO | WO2013040081 A1 | 3/2013 |
| WO | WO2017004444 A1 | 1/2017 |

OTHER PUBLICATIONS

PCT International Search Report and Written Opinion, PCT/US2016/040542, dated Sep. 16, 2016, 39 pp.

Henderson TA, Monies LD, "Near-infrared photonic energy penetration: can infrared phototherapy effectively reach the human brain?", published May 20, 2015, vol. 2015:11 pp. 2191-2208.

Swedish Laser-Medical Society, "The Low Level Laser Therapy LLLT Internet Guide, FAQ—frequently asked questions about laser therapy", 2010, 13 pp. <retrieved from: http://www.laser.nu/lllt/Faq1.htm>.

Walt, "Recommended treatment doses for Low Level Laser Therapy", Apr. 2010, 2 pp.

A N Bashkatov et al., "Optical properties of human skin, subcutaneous and mucous tissues in the wavelength range from 400 to 2000 nm", J. Phys. D: Appl. Phys. 38 (2005) 2543-2555, Jul. 22, 2005, 13 pp.

Chung et al., "The Nuts and Bolts of Low-level Laser (Light) Therapy", Ann Biomed Eng. Feb. 2012; 40(2): 516-533., Nov. 2, 2011 24 pp.

ColdLasers.org, "Wavelengths Used for Cold Laser Therapy", publication date unknown, 20 pp. <retrieved from: http://www.coldlasers.org/therapy/wavelength/>.

"Cold Laser Therapy Clinical Relevance", publication date unknown, 17 pp. <retrieved from: http://www.mccc.edu/~behrensb/documents/COLDLASERPTA236.pdf>.

White et al., "Effect of High-Intensity Laser Treatments on Chronic Pain Related to Osteoarthritis in Former Professional Athletes: A Case Series", J Mol Biomark Diagn (2017), 8:4, ISSN:2155-9929; 4 pp.

White et al., "Treatment of drug-resistant fibromyalgia symptoms using high-intensity laser therapy: a case-based review", Mar. 2018;38(3):517-523 doi: 10.1007/s00296-017-3856-5. Epub Oct. 28, 2017; 8 pp.

(56) References Cited

OTHER PUBLICATIONS

White, "An Alternative Approach to Solving the Opioid Epidemic: Expanding the Use of NonPharmacologic Techniques for Acute and Chronic Pain Management", J Mol Biol Methods 2018, 1:1, J; Jan. 4, 2018; 2 pp.

White et al., "A novel treatment for chronic opioid use after surgery", J Clin Anesth. Aug. 2017;40:51-53. doi: 10.1016/j.clinane.2017.03.046. Epub Apr. 21, 2017; 5 pp.

"Lesson 1: Production of Laser Energy", publication date unknown, 31 pp. <retrieved from: https://www.djoglobal.com/sites/default/files/Low%20Level%20Laser%20Therapy%20101.pdf>.

Wikipedia, "Near-infrared window in biological tissue", publication date unknown, 5 pp. <retrieved from: https://en.wikipedia.org/wiki/Near-infrared_window_in_biological_tissue>.

* cited by examiner

HIGH-INTENSITY LASER THERAPY METHOD AND APPARATUS

CROSS REFERENCE TO RELATED APPLICATIONS

This application is a continuation-in-part (CIP) of U.S. Non-Provisional application Ser. No. 15/157,320 filed on May 17, 2016, which is incorporated herein by reference in its entirety, which is a continuation-in-part (CIP) of U.S. Non-Provisional application Ser. No. 14/145,356 filed on Dec. 31, 2013, which is incorporated herein by reference in its entirety, which claims the benefit of U.S. Provisional Application No. 61/747,745 filed on Dec. 31, 2012, which is incorporated herein by reference in its entirety. This application is also a continuation-in-part (CIP) of U.S. Non-Provisional application Ser. No. 14/789,958 filed on Jul. 1, 2015, which is incorporated herein by reference in is entirety, which claims the benefit of U.S. Provisional Application No. 62/019,702 filed on Jul. 1, 2014, which is incorporated herein by reference in its entirety, and U.S. Provisional Application No. 62/019,708 filed on Jul. 1, 2014, which is incorporated herein by reference in its entirety.

BACKGROUND

Several non-surgical methods have been utilized in the therapeutic treatment of acute or chronic inflammation in living tissue. Some of the techniques previously utilized included the application of ultrasonic energy, electrical stimulation, high frequency stimulation by diathermy, X-rays and microwave irradiation. Techniques such as electrical stimulation, diathermy, X-ray and microwave radiation have shown some therapeutic benefit for soft tissues, however, their use has been somewhat limited because of tissue damage caused by excessive thermal effects. Consequently, the energy levels associated with therapeutic treatments involving diathermy, X-ray, microwave, and electrical stimulation have been limited to such low levels that have little or no benefit for treating acute or chronic inflammation, wounds, or joint pain. Additionally, the dosage of exposure to microwaves and X-ray radiation must be carefully controlled to avoid radiation related health problems. Ultrasonic energy is non-preferentially absorbed and can negatively affect all of the surrounding or otherwise healthy tissue.

In addition, optical energy generated by lasers has been applied for various medical and surgical purposes because of the monochromatic and coherent nature of laser light which can be selectively absorbed by living tissue depending upon certain characteristics of light of variable wavelengths and also the properties exhibited by viable cells in the irradiated tissue such as reflectivity, absorption coefficient, scattering coefficient, thermal conductivity, and thermal diffusion constant. The reflectivity, absorption coefficient, and scattering coefficient are dependent upon the wavelength of the optical radiation. Further, the absorption coefficient is known to depend upon such factors as inter band transition, free electron absorption, grid absorption (phonon absorption), and impurity absorption, which are dependent upon the wavelength of the optical radiation. Conventional lasers using low power or low level lasers using wavelengths that do not allow for any type of significant penetration into the body because of the absorption of the energy into melanin, hemoglobin, and oxy-hemoblogin. The wavelengths used by these low power and low level lasers prevent the body from absorbing the laser energy for chronic or acute inflammation or wound healing benefits. Further, water is a major component of living tissue, which has an absorption band according to the vibration of water molecules in the infrared range. In the visible range, absorption exists due to the presence of hemoglobin. Additionally, the scattering coefficient in living tissue is a dominant factor.

Therefore, for a specific tissue type, the laser light may propagate through the tissue substantially unattenuated, or may be almost entirely absorbed. The extent to which the tissue is heated and ultimately destroyed depends on the extent to which it absorbs the optical energy. It is generally preferred that the laser light be essentially transmissive in tissues that are desired not to be affected, and absorbed by the tissues which are to be affected. For example, when applying laser radiation in a tissue field that is wet with blood or water, it is desired that the optical energy not be absorbed by the water or blood, thereby permitting the laser energy to be directed specifically to the tissue to be treated.

Hence, what is needed is a laser irradiation system, method, and apparatus that is easy to use, has a simple user interface control unit, and can generate optical energy at specified or range of wavelengths, power levels, and beam profiles, among others, to treat acute or chronic inflammation, wounds, and autoimmune deficiency conditions, among others, without ablating the target tissue or surrounding tissue.

BRIEF SUMMARY

In one aspect of the disclosure described herein, a laser irradiation system, method, and apparatus is provided that can generate optical energy at a specific or a range of wavelengths, power levels, and beam profiles, among others, to treat acute or chronic inflammation, wounds, and autoimmune deficiency conditions, among others, without ablating the target tissue or surrounding tissue. More specifically, the laser irradiation method and system can percutaneously stimulate biological or cell tissue, in a non-discriminatory fashion and intracellularly, until energy homeostasis is achieved. In particular, the laser beam and optical energy of the disclosure described herein does not significantly absorb into melanin, hemoglobin, or oxy-hemoglobin. Here, the power of the laser delivered to a patient or treatment site is substantially high and dense, thereby allowing greater depths of laser light penetration and achieve higher and accelerated wound healing or inflammation healing results as compared to conventional low power laser light systems and methods. In addition, the beam profile of the disclosure described herein can be de-focused and distanced from the skin of a patient thereby preventing tissue damage and enable healing. The system, method, and apparatus of the optical irradiation cell therapy of the disclosure described herein can effect cellular activity by stimulating cell growth, increasing cell metabolism, improve cell regeneration, invoke an anti-inflammatory response, promote edema reduction, reduce fibrous tissue formation, stimulate nerve function, and stimulate the production of endorphins, among other advantages. This can further result in improve blood flow and vascularization in damaged tissue, improve and restore function of nerve cells in damaged tissue, produce natural opiates and other compounds that reduce pain and simulate healing, and direct stimulation of cellular grown and healing of soft tissues such as collagen.

In another aspect of the disclosure described herein, the laser system, method, and apparatus can include laser light wavelengths, power, and beam profiles which are optimal for penetrating the skin and getting deep into injuries as the laser light passes through cell tissue. Hence, the deep penetration of the laser light of the disclosure described herein minimizes the scatter of the laser energy by decreasing the loss of energy, and avoids excessive heat and discomfort for a patient. In addition, the laser system, method, and apparatus can operate with energy levels from approximately, 5 to 100 Watts, preferably 20 to 70 Watts. These high energy levels can further result in higher penetration and stronger biostimulation of cell tissue. The laser can safely deliver approximately 50 to 200 times the amount of continuous laser energy to damaged tissues below the skin's surface than other lower wavelength, non-thermal laser therapy devices. Further, the laser system, method, and apparatus can treat large treatment sites or large area of damaged tissue more efficiently and more uniformly because the optical components can create a laser beam profile of up to approximately 60 centimeters in diameter, preferably 30 cm, which is far larger than conventional laser systems having a 0.2 centimeter diameter. Further, the beam profile diameter can be adjusted to produce smaller diameter beams to treat smaller areas if needed which provides flexibility and a broader range of treatment options. Here, the wider beam of the present disclosure described herein can increase the amount of energy that can be safely used, and increases the tissue surface area covered at each treatment.

In one aspect of the disclosure described herein, a treatment protocol or methodology for the laser system can be determined by the type of injury and rate of healing. For example, in one embodiment, a single chronic injury may typically require an approximately 10-15 minute session per patient, whereas treatment protocols for more extensive injuries, or for multiple injuries, may require up to 30 minutes per patient or per session. Acute injuries may require treatments varying from three sessions per week to as many as two treatments per day and may be completed within a few days, or within a few weeks. Treatments may also be intermittent, with two weeks of treatment followed by two weeks of no treatments, and then repeated until the chronic pain or condition is relieved, cured, or disappears. Certain chronic conditions may require periodic maintenance treatments to prevent a reversal in the condition.

The method of the laser therapy of the disclosure described herein can further include utilizing a hand piece or hand-held portable unit having a laser source device and laser beam profile that is used for the irradiation of acute or chronically inflamed cells in a wound or tissue. Through the stimulation of photoreceptors within a cell, a cascade of intracellular metabolic reactions are initiated that move the cell towards homeostasis and in doing so resolves the acute or chronic inflammation in an expedited manner. The mechanisms include stimulating the expression and release of certain growth factors and cytokines from the cells that have infested the inflamed area, such as fibroblasts, macrophages, lymphocytes and endothelial progenitor cells. These biological mediators can bring about a proliferation of specific cell types within the wound, the inflamed tissue, or the wound or inflamed tissue's margins and coordinate the various stages of anti-inflammatory processes and wound healing, which then results in accelerated resurfacing of wounds or re-epithelialization and filling of the wound defect by granulation tissue and collagen with minimal or no scarring. The optical energy of the present disclosure described herein also increases the vascularity of the regenerating tissue that in turn results in more blood being brought to the inflamed, injured, or wound site and thus an increasing the rate of healing. Hence, there can be a resolution of metabolic deficits within cells far in excess of the effects of direct photo stimulation. Additionally, there is reduced scarring and control of superlative diseases of the skin. The laser therapy of the disclosure described herein offers an effective method, system, and apparatus for irradiating large numbers of cells with safe levels of optical energy to initiate the intracellular cascade toward homeostasis and the production of secondary effects contributing to homeostasis of adjacent or distant cells. This characteristic exponential benefit of photo stimulation is especially valuable in the treatment of acute or chronic inflammation and stimulation of the blood and immune cells of the body.

In one aspect of the disclosure described herein, a method of laser irradiation for alleviating the physical symptoms associated with acute or chronic inflammatory conditions is provided. The method can include focusing or aiming a light beam having a configured wavelength and power level on an inflamed area that is to be treated, wherein the light beam photo activates intracellular photoreceptors, thereby initiating a cascade of secondary cellular metabolic effects and normalizing cellular activity towards homeostasis. The method can further include treating surrounding reactive cells or viable cells near the inflamed area at identical time intervals so as to generate a preponderance of neutral or homeostatic cell responses en masse. In addition, the light beam can generate an increase in oxygenation in or around the inflamed area margins through angionesis or re-vascularization leading to wound healing or homeostatic cell response en masse. Here, the method can further include stimulating the production of intercellular messenger proteins and enzymes including superoxide dismutase and catalase enzymes. Here, the wavelength can include one or more wavelengths ranging from 1064 nm up to and including 1325 nm. The power level can further include one or more power levels ranging from 500 mW/cm^2 up to and including 5 W/cm^2. In addition, the light beam can further include a beam profile covering a surface area ranging from 0.1 cm^2 up to and including 60 cm^2. In addition, the light beam can also have a duration period from 30 seconds up to and including 3600 seconds. In addition, the light beam can further operate at a continuous wave mode. In addition, the light beam does not ablate cells within the inflamed treatment area or surrounding tissue area.

In another aspect of the disclosure described herein, a method of laser irradiation for alleviating the physical symptoms associated with acute or chronic inflammatory conditions is provided. Here, the method can include positioning an optical source having infrared light adjacent to a treatment site, directing the infrared light at the treatment site, configuring a wavelength for the optical source, depending on the depth and type of inflammation at the treatment site, and determining a power level for the optical source, wherein the infrared light photo activates intracellular photoreceptors at the treatment site. In addition, the method can also include configuring a wavelength in the infrared spectrum between from 1060 nm to 1325 nm, or preferably approximately 1275 nm. Also, the optical source may operate in power ranges from 750 mW/cm^2 to 1200 mW/cm^2, 350 mW/cm^2 to 1200 mW/cm^2, or 500 mW/cm^2 to 5 Watts/cm^2, or anywhere from 1 W up to and including 100 W. The optical source can also be a hand-held unit.

In another aspect of the disclosure described herein, a method of laser irradiation for alleviating the physical symptoms associated with acute or chronic inflammatory conditions is provided. Here, the method can include directing a laser unit having infrared light at damaged or inflamed cells, configuring the laser unit to a wavelength of 1100 nm to 1275 nm and a time duration, depending on the depth and type of cells to be treated, wherein the depth can range from 0.1 cm to 15 cm, configuring the laser unit to a power level of 750 mW/cm^2 to 1200 mW mW/cm^2, and configuring the infrared light to a beam profile surface area of 1 cm^2 to 60 cm^2. In addition, the method can further include operating the laser unit in a continuous wave mode and having a homogenous beam profile. Also, the method can include treating the damaged or inflamed cells in a single treatment session for a duration of time ranging from 30 seconds to about 3600 seconds, and wherein the laser unit operates below the photo ablation threshold of the cells being treated.

In another aspect of the disclosure described herein, a method of alleviating the physical symptoms associated with acute or chronic inflammatory conditions which can include receiving a repeat cycle mode for emitting a non-invasive and non-ablative laser beam having a wavelength. The method can further include receiving an emission time for the non-invasive and non-ablative laser beam, receiving an stop time for the non-invasive and non-ablative laser beam, receiving a power output for the non-invasive and non-ablative laser beam, receiving a frequency for the non-invasive and non-ablative laser beam, and receiving a repeat counter value for the repeat cycle mode operation. In addition, upon receiving the repeat cycle mode, emission time, emission pause time, power output, frequency, and repeat counter value, then emitting the non-invasive and non-ablative laser beam. Here, the wavelength and power are configured such that they photo activate intracellular photoreceptors, thereby initiating a cascade of secondary cellular metabolic effects and normalizing cellular activity towards homeostasis. In addition, the non-invasive and non-ablative laser beam can further include treating surrounding reactive cells or viable cells near the inflamed area at identical time intervals so as to generate a preponderance of neutral or homeostatic cell responses en masse. In addition, the non-invasive and non-ablative laser beam generates an increase in oxygenation in or around the inflamed area margins through angionesis or revascularization leading to wound healing or homeostatic cell response en masse. Further, the emitted non-invasive and non-ablative laser beam can also include stimulating the production of intercellular messenger proteins and enzymes including superoxide dismutase and catalase enzymes. Here, the wavelength can also include one or more wavelengths ranging from 1064 nm up to and including 1325 nm. The power output can further include one or more power levels ranging from 500 mW/cm^2 up to and including 5 W/cm^2, or from 1 W up to and including 100 W. In addition, the light beam can further include a beam profile covering a surface area ranging from 0.1 cm^2 up to and including 60 cm^2. Here, the emission time can further include a duration period from 3 seconds up to and including 3600 seconds. The non-invasive and non-ablative laser beam can be a continuous wave operation. In addition, the non-invasive and non-ablative laser beam does not ablate cells within the inflamed treatment area or surrounding tissue area.

In another aspect of the disclosure described herein, a method of alleviating the physical symptoms associated with acute or chronic inflammatory conditions is disclosed. Here, the method can include receiving a mode of operation, wherein the mode of operation comprises a continuous wave, pulsed, or semi-continuous wave mode of operation to emit a laser beam having a wavelength ranging from 1060 nm up to and including 1325 nm, receiving a power output for the laser beam, and receiving a frequency for the laser beam. The method can also include upon receiving the mode of operation, power output, and frequency, then emitting the laser beam having the wavelength ranging from 1060 nm up to and including 1325 nm. The method can further include the laser beam having power ranges from 750 mW/cm^2 to 1200 mW/cm^2. The method can also include the laser beam having power ranges from 350 mW/cm^2 to 1200 mW/cm^2. In addition, the laser beam may also have power ranges from 500 mW/cm^2 to 5 Watts/cm^2. Further, the power output ranges for the laser beam can be from 1 W up to and including 100 W. In addition, the power output ranges for the laser beam can also be from 1 W up to and including 42 W.

In another aspect of the disclosure described herein, a method of laser irradiation for alleviating the physical symptoms associated with acute or chronic inflammatory conditions is disclosed. The method can include directing a laser beam from a laser unit in a continuous wave operation having a wavelength of approximately 1275 nm and a power output level in the range of from one (1) Watt up to and including 75 Watts on an inflamed area that is to be treated, such that the laser beam penetrates the inflamed area in the range of from 0.1 cm to 30 cm. Here, wherein the laser beam from the laser unit is configured to activate intracellular photoreceptors, thereby initiating a cascade of secondary cellular metabolic effects and normalizing cellular activity towards homeostasis. In addition, the laser beam is directed from a laser probe positioned from four (4) to six (6) inches away from the surface of the skin or region to be treated. Alternatively, the laser beam may also be directed from a laser probe positioned from approximately 12 in. to 16 in. away from the surface of the skin or region to be treated. In addition, the method can include wherein a duration for a treatment session can be for at least approximately 30 minutes.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

Figure 1:
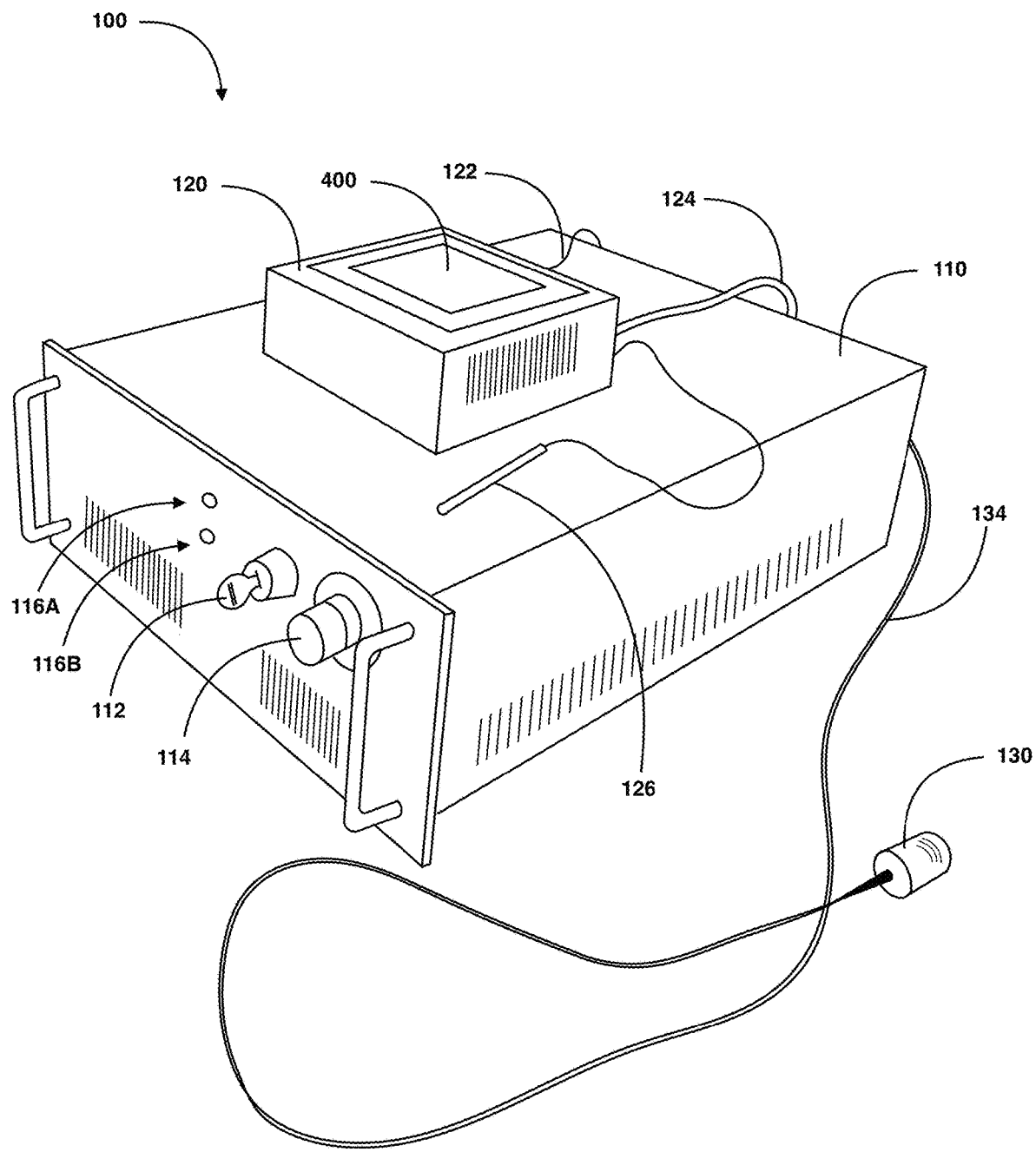
FIG. 1 illustrates a perspective view of one non-limiting embodiment of the non-invasive and non-ablative laser therapy apparatus of the disclosure described herein.

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

In one implementation of the disclosure described herein, a display page may include information residing in the computing device's memory, which may be transmitted from the computing device over a network to a central database center and vice versa. The information may be stored in memory at each of the computing device, a data storage resided at the edge of the network, or on the servers at the central database centers. A computing device, controller, or control unit, or mobile device may receive non-transitory computer readable media, which may contain instructions, logic, data, or code that may be stored in persistent or temporary memory of the mobile device, or may somehow affect or initiate action by a mobile device. Similarly, one or more servers may communicate with one or more mobile devices across a network, and may transmit computer files residing in memory. The network, for example, can include the Internet, wireless communication network, or any other network for connecting one or more mobile devices to one or more servers.

Any discussion of a computing, control unit, or mobile device may also apply to any type of networked device, including but not limited to mobile devices and phones such as cellular phones (e.g., an iPhone®, Android®, Blackberry®, or any 'smart phone'), a personal computer, iPad®, server computer, or laptop computer; personal digital assistants (PDAs) such as a Palm-based device or Windows® CE device; a roaming device, such as a network-connected roaming device; a wireless device such as a wireless email device or other device capable of communicating wireless with a computer network; or any other type of network device that may communicate over a network and handle electronic transactions. Any discussion of any mobile device mentioned may also apply to other devices, such as devices including Bluetooth®, nearfield communication (NFC), infrared (IR), and WiFi functionality, among others.

Phrases and terms similar to "software", "application", "app", and "firmware" may include any non-transitory computer readable medium storing thereon a program, which when executed by a computer, causes the computer to perform a method or function.

Phrases and terms similar "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Phrases and terms similar to "portal" or "terminal" may include an intranet page, internet page, locally residing software or application, mobile device graphical user interface, program display or screen, or digital presentation for a user or operator. The portal may also be any graphical user interface for accessing various modules, features, options, and/or attributes of the disclosure described herein. For example, the portal can be a web page accessed with a web browser, mobile device application, or any application or software residing on a computing device or control unit.

FIG. 1 illustrates a prospective view for one non-limiting embodiment of the non-invasive and non-ablative laser therapy apparatus 100 of the disclosure described herein. In particular, the laser therapy apparatus 100 includes a main unit 110 component for generating a non-invasive and non-ablative laser beam and graphical user interface control unit 120 for allowing a user to control the operation of the laser therapy apparatus 100. Here, controller 120 is connected to and communicates bi-directionally with main unit 120 via communication line cable 122 and powered via cable 124. However, it is contemplated within the scope of the disclosure described herein that controller 120 may also communicate wirelessly with unit 110 and may also be powered wirelessly. Further, controller 120 and unit 110 may also be connected to a separate computing device (not shown) for transferring, uploading, or downloading software, firmware, various data, operational parameters, patient information, log history, and the like. In addition, either controller 120 or unit 110 may be programmed, pre-programmed, or controlled from another computing device, network server, client terminal, or the like. Controller 400 also includes a touch-screen graphical user interface 400 allowing an operator to operate apparatus 100, which will later be discussed in detail in this disclosure. In addition, the graphical user interface 400 of controller unit 120 may be operated via either touch input or via a stylus or input device 126.

Figures 2A, 2B:
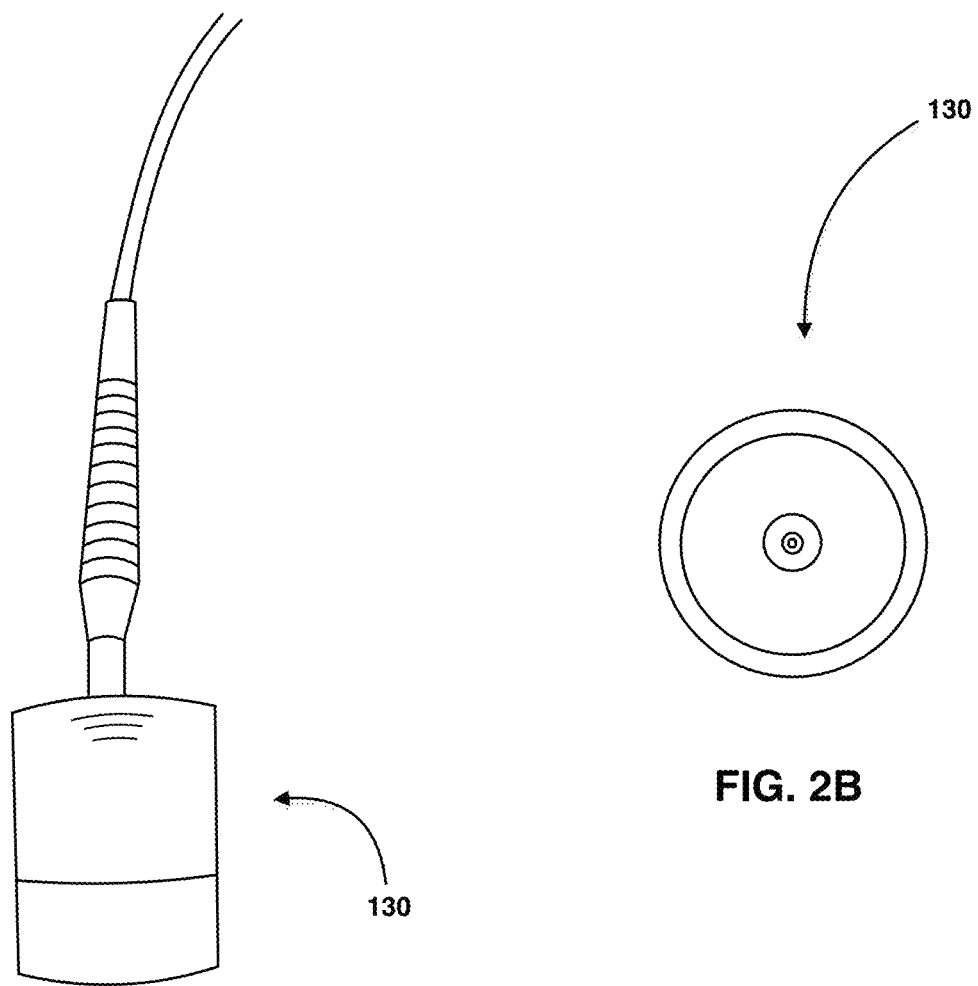
FIG. 2A illustrates a top overhead view of a guide or light source for the laser therapy apparatus of the disclosure described herein.
FIG. 2B illustrates a front interior view of the guide for the laser therapy apparatus of the disclosure described herein.

Still referring to FIG. 1, apparatus 100 further includes laser light source, hand-piece, hand-held unit, or laser guide unit 130 for directing a laser beam and beam profile on to an area of a user or patient, wherein guide unit 130 is connected to main unit 110 via optic cable line or communication line 134. Here, in one embodiment, a laser therapy type, operating time, cycles, power, and beam profile can be controlled via control unit 120 and main unit 110. In addition, guide 130 may also have the capability to alter, modify, or manipulate the beam profile of the laser. Still referring to FIG. 1, main unit 110 further includes a pair of side handles for carrying the unit and ventilation areas on its sides. In addition, main unit 100 includes an on/off key switch 112 for powering the unit on and off, an emergency stop switch or knob 114 for immediately ceasing operation of the laser beam via guide 130, a ready light indicator 116B indicating that the unit is ready for emitting laser light, and an emission light indicator 116A indicating that the guide 130 is now emitting laser light. Here, FIGS. 16-18B also illustrate various photographic views of the laser apparatus 100. FIG. 2A illustrates a top overhead view of guide 130 and FIG. 2B illustrates an interior front view of guide 130.

Figure 3A:
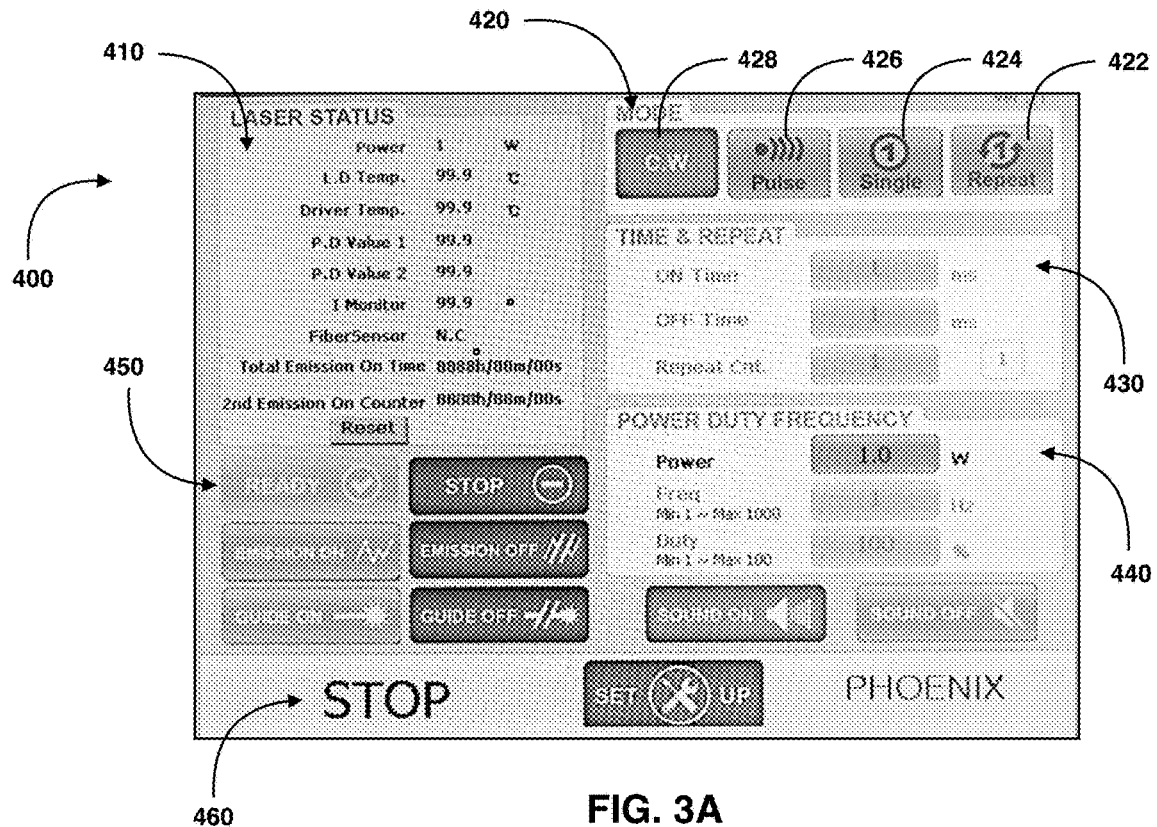
FIGS. 3A-7B illustrate a graphical user interface for the laser therapy apparatus of the disclosure described herein.
Figure 3B:
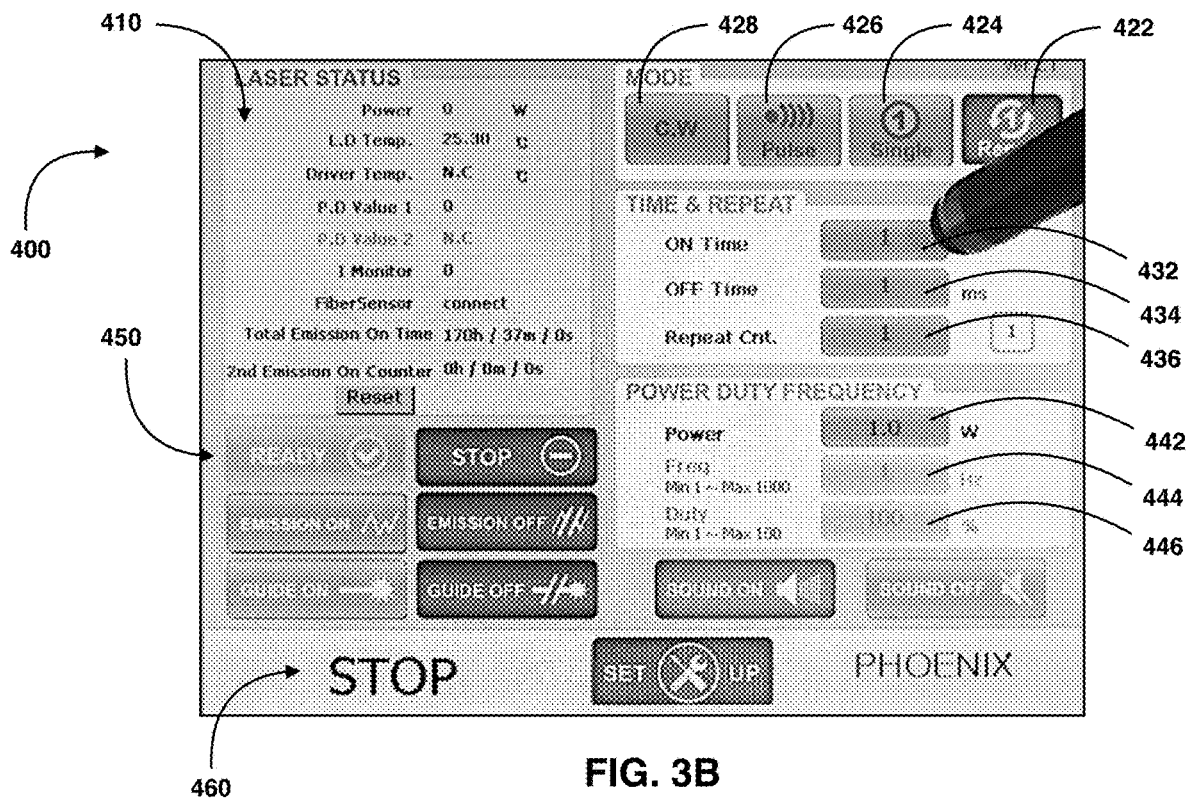
Figure 4A:
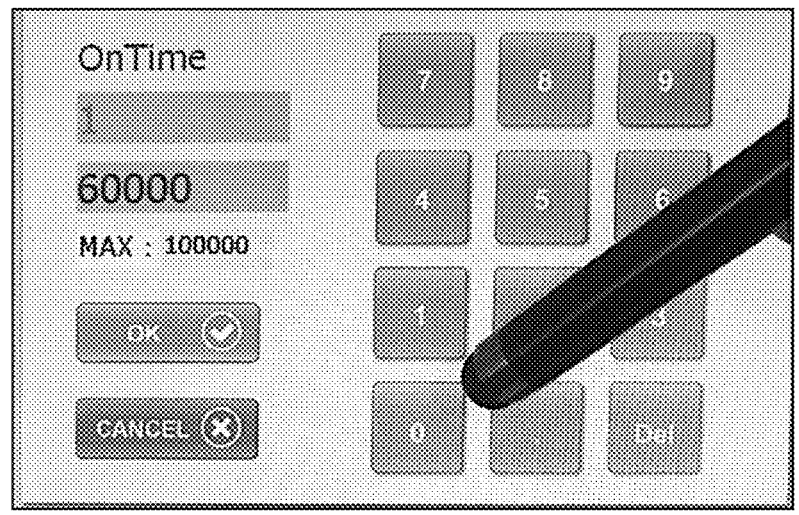
Figure 4B:
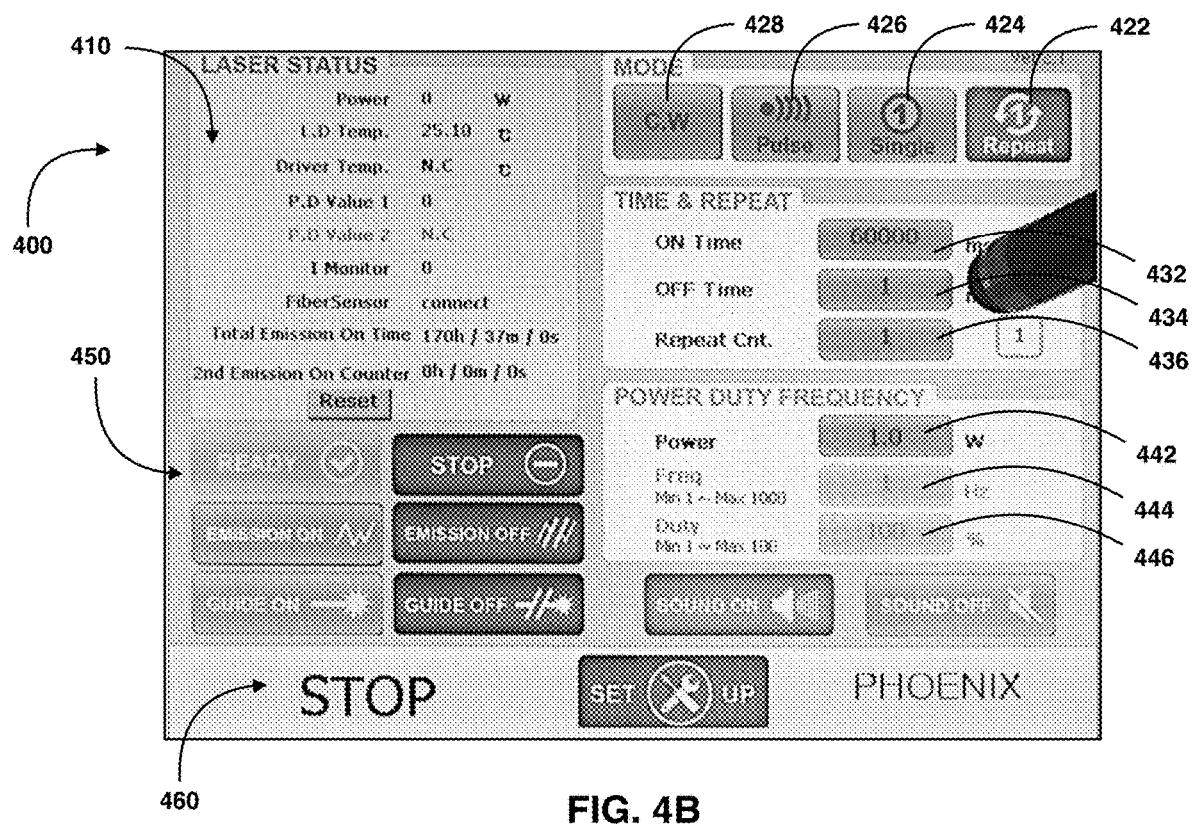

FIGS. 3A-7B illustrate various graphical user interface screens, displays, or portals for operating laser therapy apparatus 100. Referring, to FIG. 3A, user interface display 400 can include window or tab region 410 for indicating various operating parameters for apparatus 100 and the laser, including but not limited to Power, L.D. Temperature, Driver Temperature, P.D. Values, I Monitor, FiberSensor, Total Emission On Time, and 2nd Emission On Counter. In addition, tab region 450 can indicate and provide a status as to when the apparatus is "Ready" mode, "Stop" or stopped mode, laser emission is in ON mode, laser emission is in OFF mode, when guide 130 is ON, and when guide 130 is OFF. A tab region 460 can also indicate whether the laser operation is in "STOP" more or in on "LASING" mode. Further, a tab region 420 can provides for selection of various modes of operation for the laser, including continuous wave (C.W.) operation 420, pulse or pulsing operation 426, one single cycle operation 424, and a repetitive cycle operation 422 wherein the repeat cycle can be configured by an operator. Specifically, when repeat operation 422 is selected, tab region 430 will be wherein an operator can input a laser ON time duration parameter 432, a laser OFF time duration parameter 434, and a laser repeat count parameter 436. In addition, the user interface includes tab region 440 for inputting power and frequency parameters for the laser beam, such as power 442, frequency 444, and duty 446.

Figure 5A:
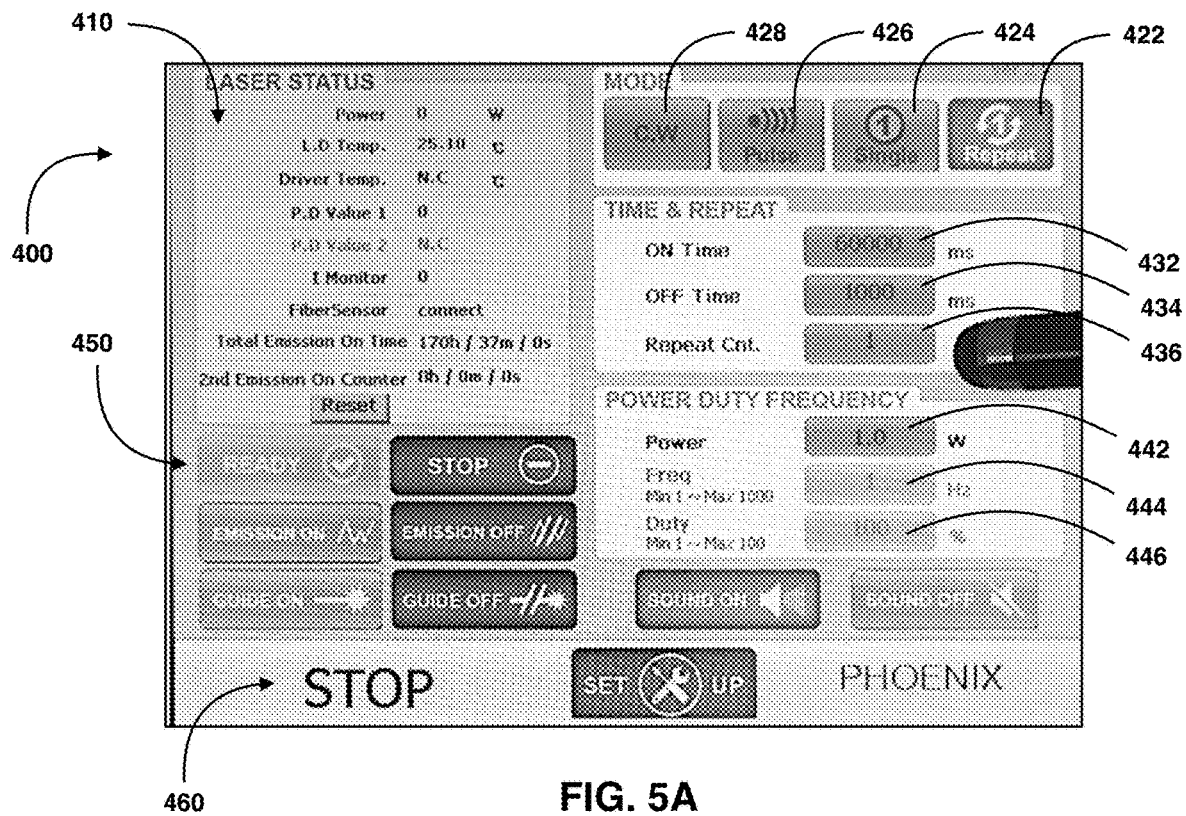
Figure 5B:
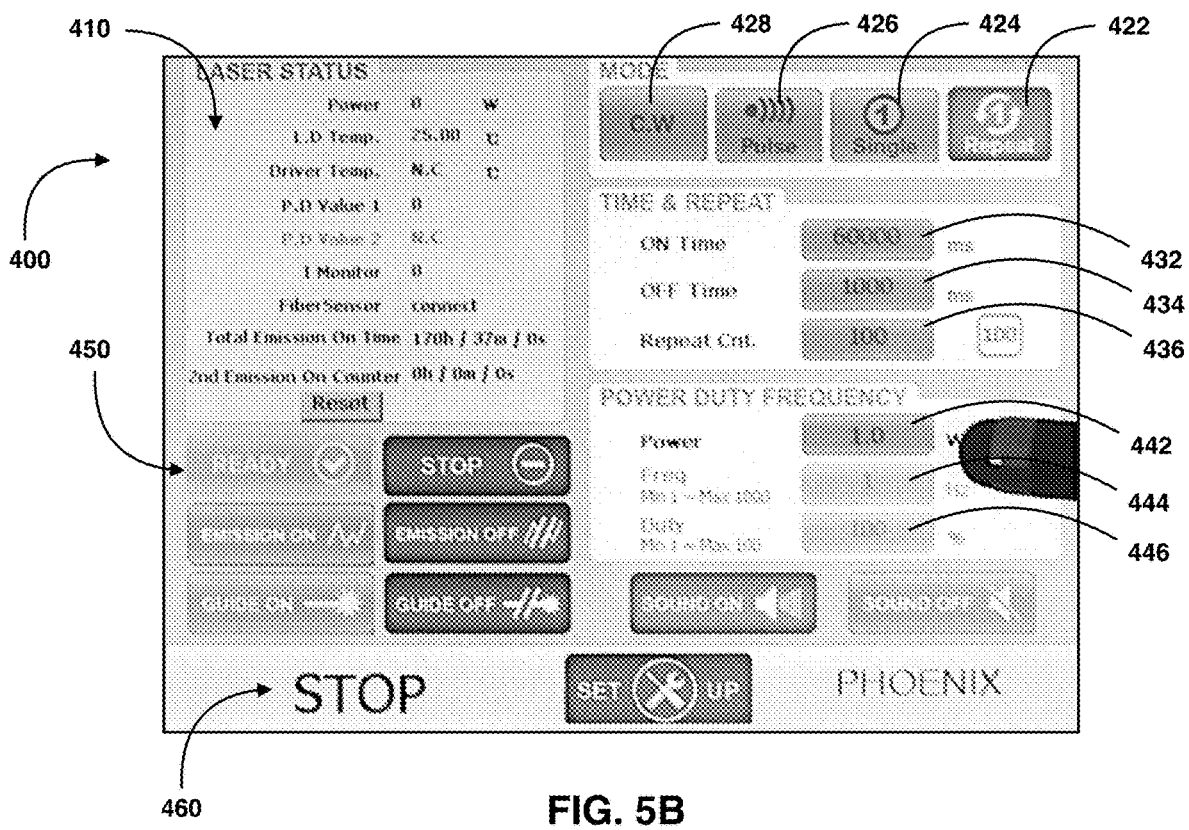
Figure 6A:
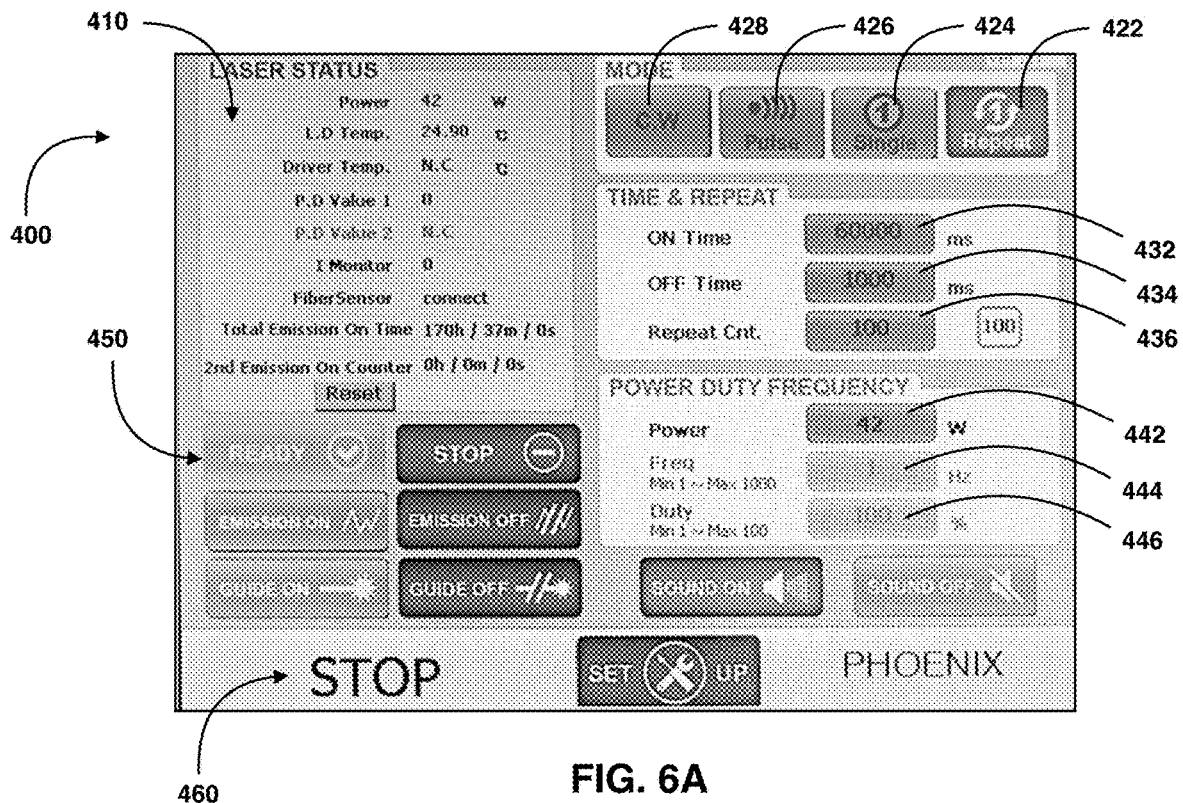
Figure 6B:
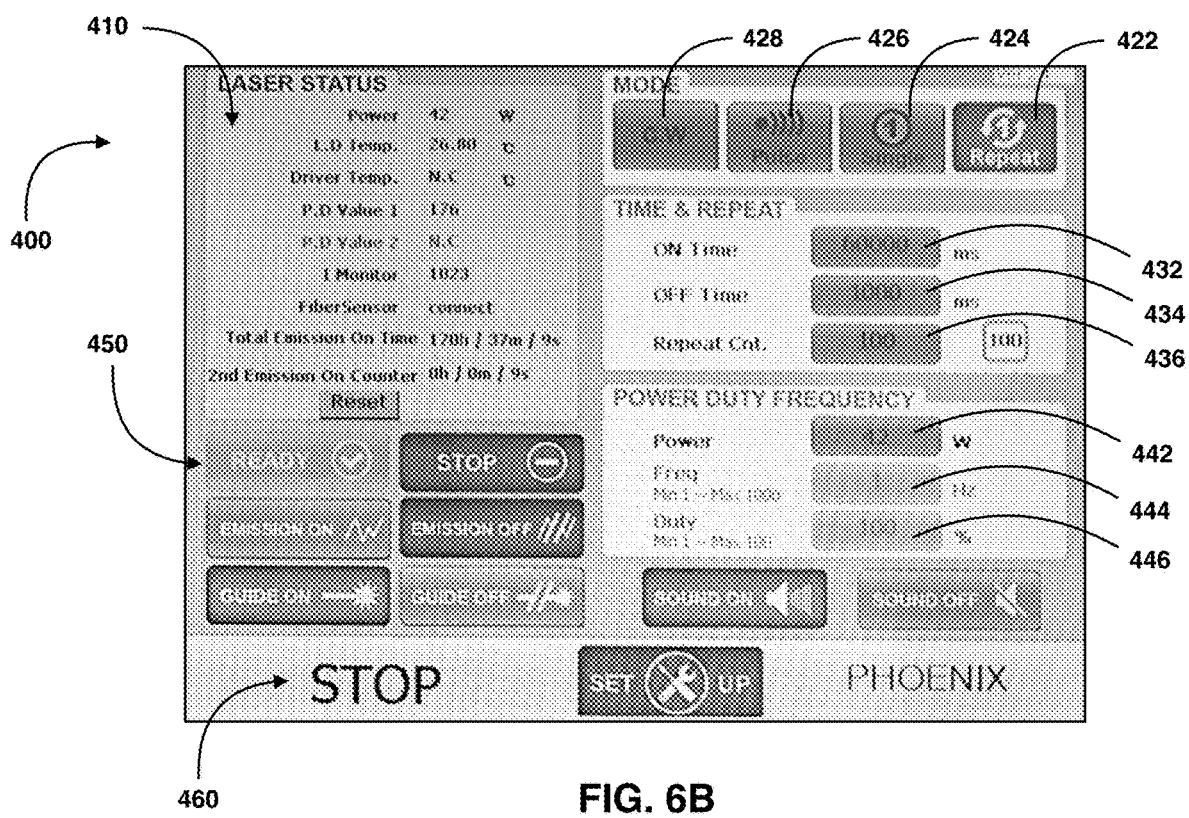

Referring to FIGS. 3A-4B, when repetitive mode operation 422 is selected, then an operator or user can input various parameters via tab regions 430 and 440. Here, the repetitive mode operation or repeat cycle operation can also be referred to herein as semi-continuous wave operation or quasi-continuous wave operation. Specifically, an operator or user can input laser ON time via input box 432, which will then guide to operator to the display of FIG. 4A, wherein the time value (in milliseconds) can be entered and received by the control unit 120. Next, by selecting "Ok", then the operator will be taken back to the screen in FIG. 3B. Similarly, the operator can input an the amount of time that the laser will be in OFF mode, such as a pause or stop time, or the time needed for the operator to move the guide body over the next appropriate area of a patient or user's body to receive the laser, as shown and discussed with respect to FIGS. 10A-13. Specifically, while in mode 422, the ON time represents the time the laser is working focused on a particular area of a patient or user's body (as shown in FIGS. 10A-13) and the OFF time represents the time needed for the operator to move the laser guide 130 to another area or treatment point of the patient or users body until the apparatus goes back to ON mode, thus repeating this cycle for defined or pre-defined number of times via input box 436. For example, FIG. 5B illustrates one exemplary embodiment for one treatment session with the laser apparatus of the disclosure described herein in the repetitive operation mode, illustrating sample value for fields 432, 434, and 436. In addition, if single mode operation 424 is selected, then fields 432-436 may also be inputted and populated. In other embodiments, control unit 120 may be configured to pre-populate or have pre-defined values for any of fields 432-436 depending on the mode selected, laser therapy treatment session type, treatment session duration, body area to be treated, patient type, patient information, or other pre-defined or pre-configured settings.

Still referring FIGS. 3A-4B, the operator may also input the laser beam parameters for power, duty, and frequency via tab region 440. Specifically, the laser power (in Watts) can be entered via input box or field 442 and can range anywhere from one (1) Watt up to and including 100 Watts, preferably 42 Watts. Moreover, the power setting 442 can be anywhere from 1 W up to 42 W. Alternatively, the power setting 442 for the beam output may also be from 1 W up to 75 W, or 37 W up to 75 W, or 1 W up to 100 W. The aforementioned power settings 442 would be administered at anywhere from 1064 nm up to and including 1325 nm, preferably 1 W, 42 W, 74 W, or 75 W at approximately 1275 nm, or from around 1270-1280 nm. Further, the size, diameter, and surface area of the beam profile can depend directly on the entered, selected, or pre-defined power output via field 442. Still referring to tab region 440, the laser frequency (in Hz) can be entered via input box or field 444 and can range anywhere from 1 Hz up to and including 1000 Hz, such as one (1) Hz. The laser duty (in percentage) can be entered via input box or field 446 and can range from 1% up to and including 100%, preferably 100%. However, it is contemplated within the scope of the disclosure herein that any other values may be used for either of input fields 442, 444, or 446. Alternatively, control unit 120 may be configured to pre-populate or have pre-defined values for any of fields 442, 444, or 446 depending on the mode selected, laser therapy treatment session type, treatment session duration, body area to be treated, patient type, patient information, or other pre-defined or pre-configured settings. Here, once fields 432-436 and 442-446 are manually populated by the operator or any combination of which is automatically pre-populated by the control unit, then the apparatus is ready to begin the treatment session. In particular, within region 450 the Ready mode can be selected by the operator or automatically highlighted or initiated by the control unit, the Emission On mode can be selected by the operator or automatically highlighted or initiated by the control unit, and the Guide On mode can be selected by the operator or automatically highlighted or initiated by the control unit. Once, any one or more of modes Ready, Emission On, and/or Guide On are highlighted, initiated, turned on, or selected, then the cycle ON Time (from field 432) and OFF time (from field 434) commences according to the defined number of cycles (from field 436) for the semi-continuous wave or quasi-continuous wave repeat mode operation 422. In addition, a status indicator can be provided indicating how many cycles have been performed thus far.

Figure 7A:
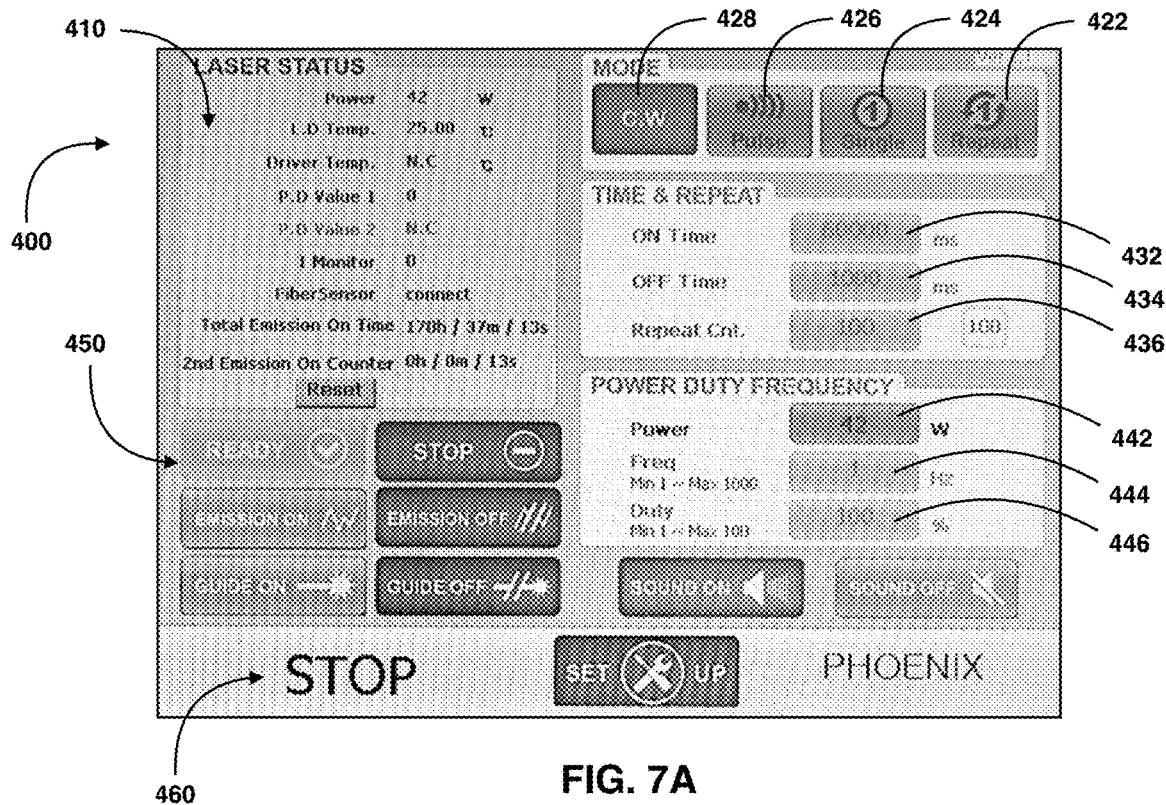
Figure 7B:
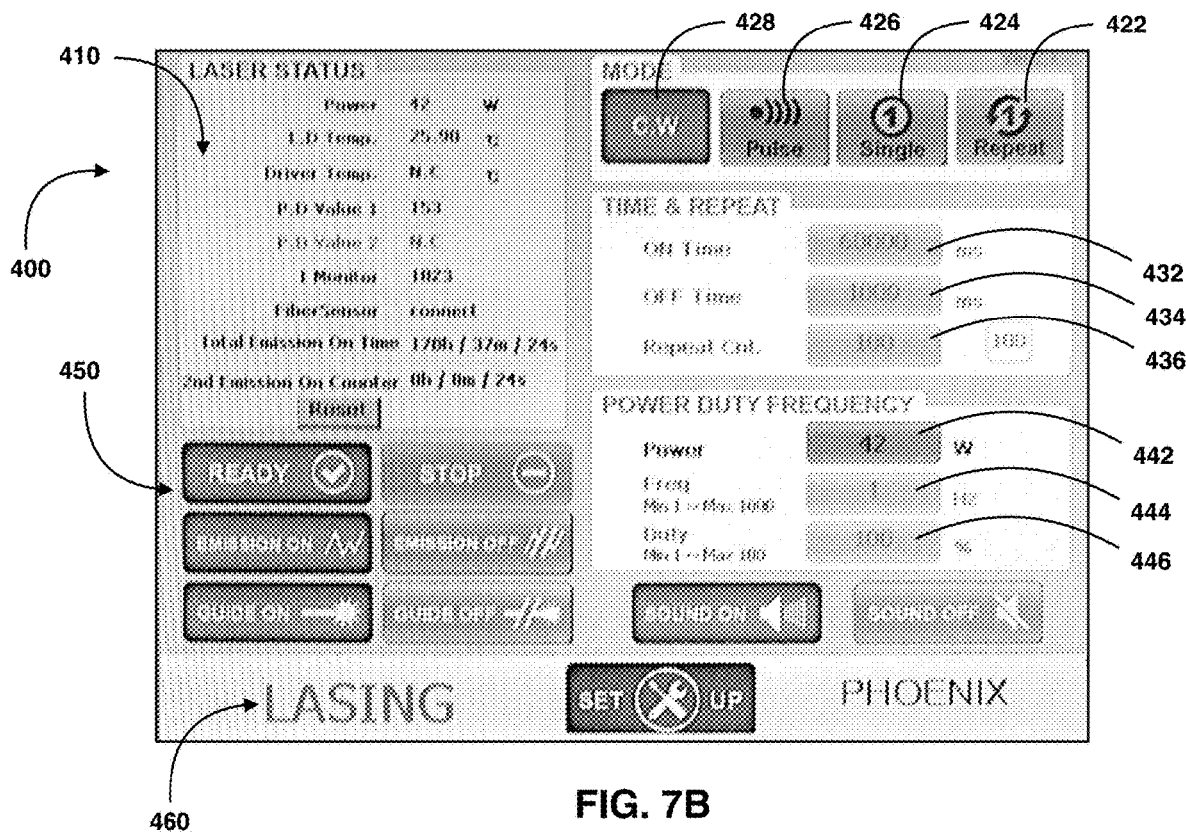

Referring to FIGS. 3A-7B, the operator of the apparatus may also have the option to select the continuous laser beam wave (C.W.) mode 428, wherein power, duty, and frequency values can be inputted or populated in fields 442, 444, and 446 in tab region 440. Similarly, if a pulsing laser beam or pulse mode 426 is selected, then fields 442, 444, and 446 can be inputted or populated in tab region 440. Similarly, if a single laser beam mode 424 is selected, then fields 442, 444, and 446 can be inputted or populated in tab region 440. Here, FIG. 7B illustrates one exemplary embodiment of the user interface display screen illustrating areas 450 and area 460 in Ready, Emission On, Guide On, and Lasing mode operation, wherein such operations can be shown for any of modes 422, 424, 426, or 428.

In one embodiment, the laser therapy of the disclosure described herein is intended to non-invasively and non-ablatively treat soft tissue or hard tissue, such as cartilages, for acute or chronic inflammation or wounds. The method and apparatus can include utilizing a laser or optical energy source, guide, and/or output device to irradiate inflamed or damaged cells in a wound. In one embodiment, the laser device can include a hand-held unit, hand piece, or guide that is made to be portable; however, it is contemplated within the scope of the disclosure described herein that the laser device may also be a fixed or mobile unit having a plurality of components. For example, a mounting structure can be used such that the hand piece may be used from a fixed position.

In a further embodiment of the disclosure described herein, there may be multiple sequential surface area irradiations in a uniform, discrete, continuous, pulsed manner, or a combination thereof, to expose the maximum number of underlying inflamed or affected "reactive" cells. This sequential irradiation method can further include major blood cell concentrations in vascular structures as well as specific organ sites. Here, special attention can be directed to the irradiation of all or specific surrounding structures around acute or chronic inflammatory processes, including but not restricted to chronic ulcers, decubitus ulcers, diabetes related ulcers, acne vulgris certain types of psoriasis and acute or chronic abscesses. In addition, such treatment methods by the laser device of the disclosure described herein can be manual, automated, or pre-programmed. For example, a health practitioner may manually operate and direct the laser beam of the laser device on one or more areas to be treated. Alternatively, the laser device may automatically be pre-programmed to operate, or move about, to direct the laser beam on one or more areas of a patient for specific predefined time periods, continuous or pulsed operation, wavelengths, beam profiles, and power outputs, among others.

Figure 8:
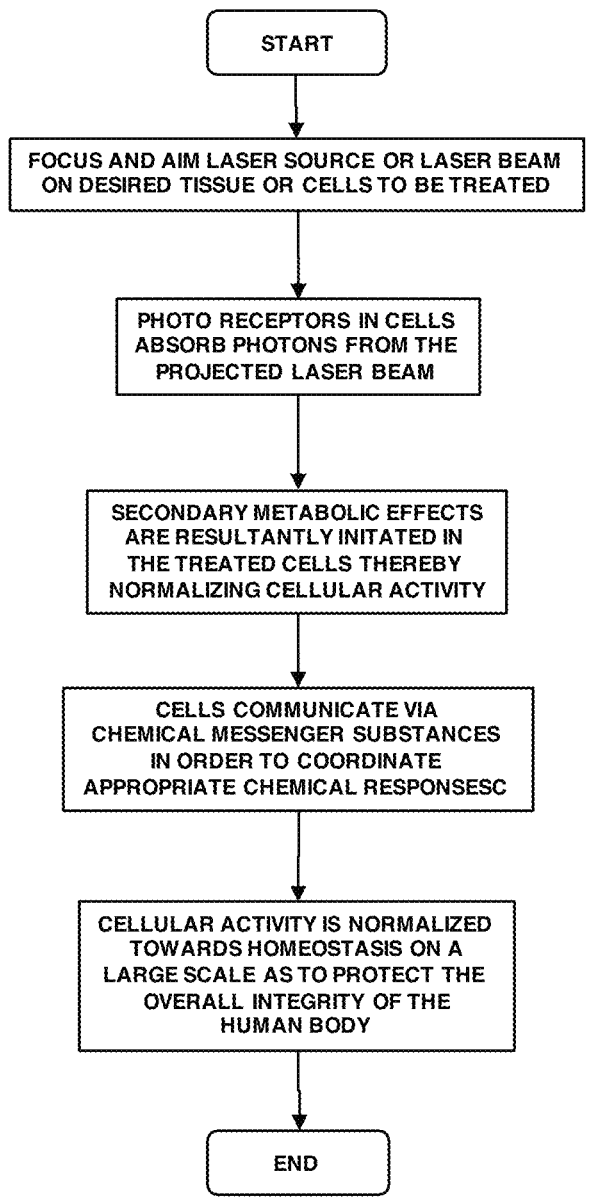
FIG. 8 illustrates one non-limiting embodiment of a block diagram or flowchart describing the cellular regeneration process of treated cells.

Referring to FIG. 8, laser irradiation is utilized to alleviate the physical symptoms associated with acute or chronic inflammatory conditions or wound healing. For example, symptoms such as pain and discomfort and specific organ involvement are the result of acute or chronic inflammation or infection of a wound. In one embodiment of the disclosure described herein, photo activation of intracellular photoreceptors initiates a cascade of secondary cellular metabolic effects, normalizing cellular activity towards homeostasis. This homeostasis is a fragile balance related to the reactive condition of adjacent cells. It is preferred to treat as many reactive or viable cells as possible at or near the same time interval in or near the wound area so as to generate a preponderance of neutral or homeostatic cell responses en masse. Further, the amount of time and intensity of treatment can be determined by the character of the cells to be treated, the depth of penetration desired, the chronicity of the condition, and the physical condition of the patient. Any number of factors in addition to those described above may be used to determine the operating levels of the hand piece such that it is operated below the photo ablation threshold of the tissue. The use of the laser therapy of the disclosure described herein acts to stimulate cellular regeneration, stabilize cell membranes, stabilize the indices of red blood cell deformation, increase lymphocyte counts, stimulate intracellular metabolism through mitochondrial photoreceptors, and stimulate the production of intercellular messenger proteins and enzymes, specifically superoxide dismutase and catalase enzymes. Additionally, there is immediate increase in membrane permeability of nerve cells and regeneration of Schwann cells lining the nerves. RNA and subsequently DNA production is enhanced. Singlet $O^2$ is also produced which further contributes to cellular regeneration.

When these responses are exaggerated or erroneous as in the case of acute or chronic inflammation a violent cascade of cellular reactions contributes to biological changes which result in ongoing messenger signaling and elicits ongoing reactive cellular metabolic responses. Here, the rapid communication between immune and body cells brings about a proliferation of specific cell types within the inflamed area or its margins and orchestrate the various stages of anti-inflammatory processes through photo activation of cellular photoreceptors of large masses of cells a homeostatic intracellular metabolism and messaging. As intercellular messaging indicates homeostatic status, the reactive status of cells stabilizes through the various intracellular secondary metabolic effects and normalcy resumes.

Figure 9:
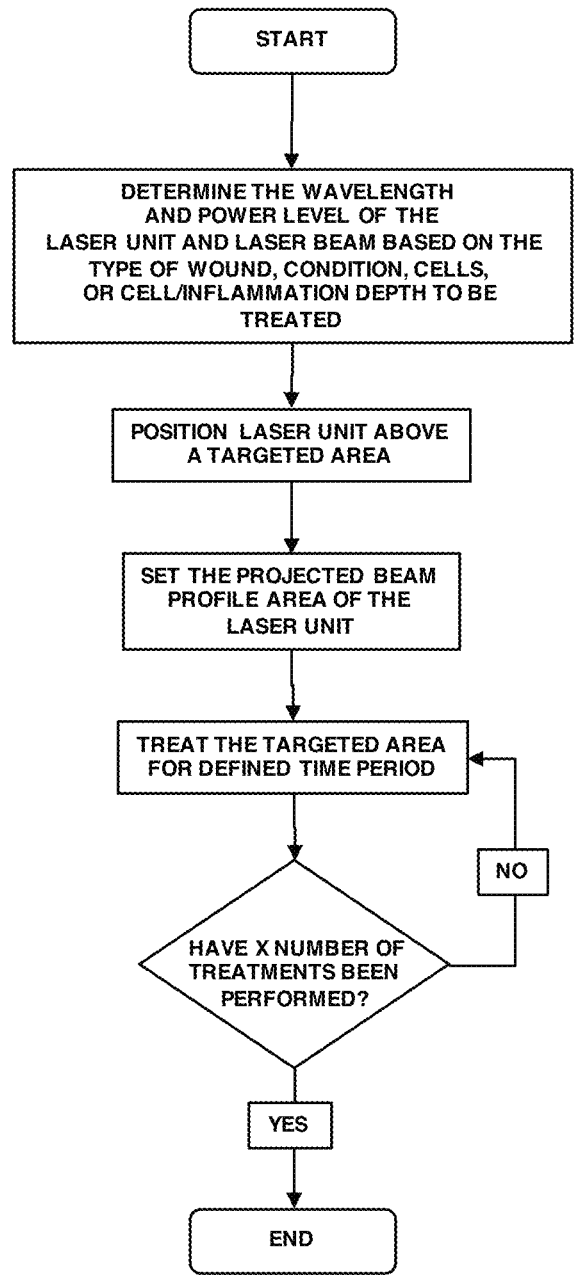
FIG. 9 illustrates one non-limiting embodiment of a block diagram or flowchart describing the treatment process of a wound using the method of the disclosure described herein.
Figure 10A:
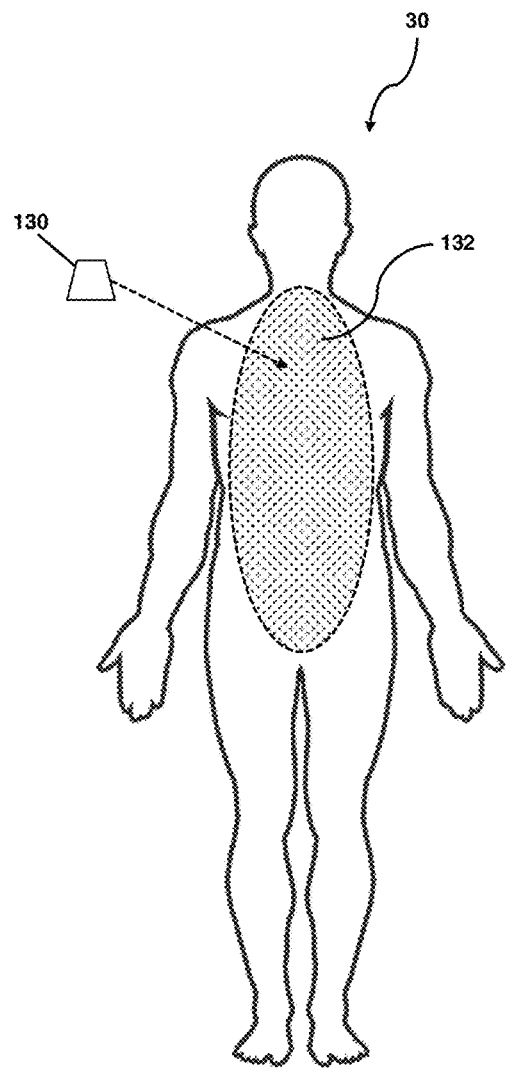
FIG. 10A illustrates one non-limiting embodiment front view diagram of a patient depicting a treatment method using one laser light source having one beam profile for treating a large treatment or surface area.
Figure 10B:
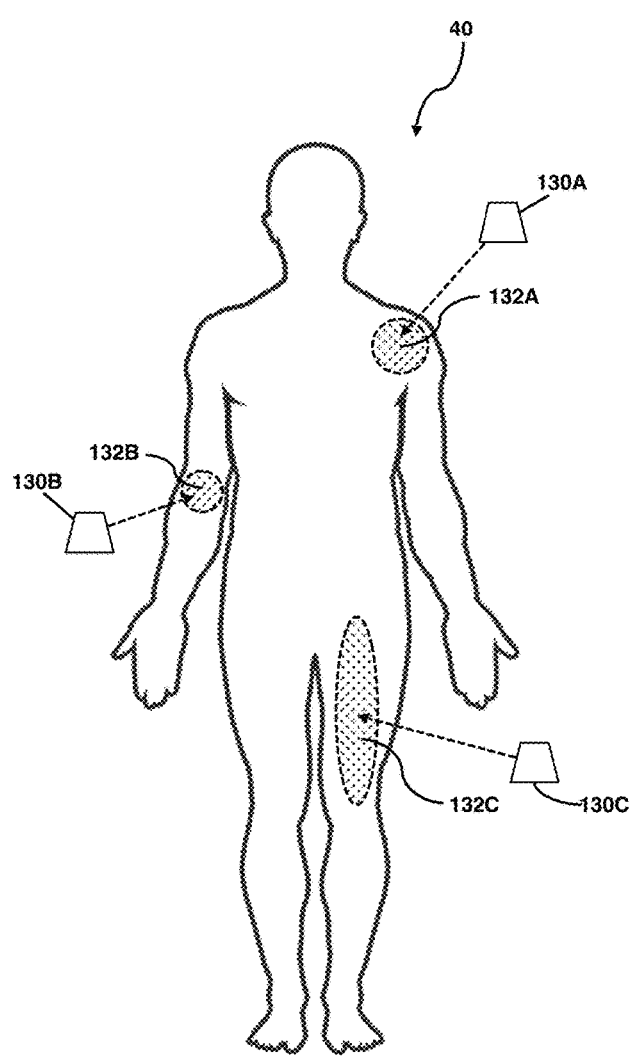
FIG. 10B illustrates another non-limiting embodiment front view diagram of a patient depicting a treatment method using plurality of laser light sources being used to treat a plurality of treatment sites.

Referring to FIG. 9, in one embodiment, the hand piece or laser device can be directed at damaged or inflamed cells in the wound and the laser device is configured to the appropriate wavelength and power level. Here, the wavelength, power level, beam profile, duration, and other operating parameters of the laser of the hand piece can depend on the depth and type of cells being treated, among other factors. Other factors can include but are not limited to the skin type, melanin levels, ethnical background/ancestry of the patient, past conditions, prior medical history, severity of the wound or inflammation condition, medications taken, among others. Here, laser or optical energy of the laser device and hand piece of the disclosure described here can be ideally operated in the infrared spectrum at wavelengths ranging from 1060 nm up to and including 1325 nm. However, it is contemplated within the scope of the disclosure described herein that the laser device or hand piece may be operated at any other wavelength. In addition, the laser or optical energy of the laser device or hand piece of the disclosure described herein can be operated at any level of power, with preference given to the 750 mW to 2.8 Watts/cm^2 range and/or 500 mW to 5 Watts/cm^2 range. However, it is contemplated within the scope of the disclosure described herein that the laser device or hand piece may also be operated at any power level. For example, in embodiment of the disclosure described herein, the hand piece and laser device can be operated at a wavelength of 1275 nm or 1064 nm and within the 750 mW to 2.8 Watts/cm^2 range.

In other embodiments, the laser device may be operated at or the laser therapy treatment method parameters include but not limited to any one or more wavelengths from 1060 nm to 1325 nm, at any one or more power levels from 500 mW/cm^2 to 5 Watts/cm^2, at any time duration from 5 seconds up to 3600 seconds, continuous or pulsed laser operation, at one or more beam profiles from an area of 0.1 cm^2 to 60 cm^2 or 0.1 cm to 60 cm in diameter, or any combination of the parameters thereof, to treat cells from any one or more depths of 1 cm to 30 cm. Here, the hand held laser can also be configured to operate in a continuous or pulsed mode at any of the aforementioned wavelengths, power levels, and beam profiles. In addition, the laser device or hand piece can have a homogenous beam profile between one square centimeter and sixty square centimeters of surface area irradiation. Here, the area of surface irradiation plays an important role to the efficient radiation of a high volume of cells concurrently. As previously noted it is felt necessary to overcome cell numbers in a "reactive" state to benefit from the secondary benefits of photo stimulation involving chemical messaging between cells. The projected beam may also be non-homogenous and may have a projected surface area less than or greater than the range described above. Further, in one embodiment of the disclosure described herein, the treatment duration range for a single treatment session can between 30 seconds to 3600 seconds, or from 3 hours up to 24 hours. However, it is also possible for the treatment duration to be shorter or longer.

For each treatment, the hand piece or laser device can be configured such that it is operated below the photo ablation threshold of the tissue being treated. Photo stimulation through the use of the laser device and method of the disclosure described herein at the disclosed parameters of wavelengths, power levels, beam profiles, and durations, among others, specifically activates the photoreceptors of cell membranes. This initiates Adenosine-triphosphate (ATP) production in the mitochondria of these reactive or viable cells. The increased cellular energy in the form of ATP is then used by the cell to finance cellular metabolic needs as well as other cellular functions such as angiogenesis, cellular regeneration, increase fibrosis and stimulation of the production of intercellular messenger proteins and enzymes as the cells moves metabolically towards homeostasis which is determined by genetic determination of cell type and function. In addition, the homeostatic cells can continuously communicate with adjacent and even distant cells by sending and receiving chemical messenger substances. These messenger substances relate cell status to adjacent and distant cells and coordinate appropriate chemical responses to protect the integrity of the body overall.

Further, platelets in a wound and surrounding area can produce platelet-derived growth factor (PDGF) that stimulates fibroblast proliferation during early as well as late phase of wound healing by promoting collagenase production from fibroblasts for wound remodeling that results in decrease or minimal scarring. This homeostasis is a fragile balance related to the reactive condition of adjacent cells. It is preferred to treat as many reactive or viable cells as possible at or near the same time interval in or near the wound so as to generate a preponderance of neutral or homeostatic cell responses en masse. In one embodiment, the amount of time and intensity of treatment is determined by the character of the cells to be treated, the depth of penetration desired, the chronicity of the wound, and the physical condition and age of the patient. Any number of factors in addition to those described above may be used to determine the operating levels of the hand piece such that it is operated below the photo ablation threshold of the tissue.

In one embodiment, the use of high powered non-invasive optical energy in the disclosure described herein acts to treat acute or chronic wounds through increased circulation, cellular regeneration, stabilize cell membranes, stabilize the indices of red blood cell deformation, increase fibrosis, stimulate intracellular metabolism through mitochondrial photoreceptors, and stimulate the production of intercellular messenger proteins and enzymes. Further, there can be an immediate increase in membrane permeability of nerve cells and regeneration of Schwann cells lining the nerves. RNA and subsequently DNA production is enhanced. All these enhanced physiological events lead to accelerated wound closure rates, increased tensile strength, and decrease or minimal scarring. Here, cellular responses in the case of an acute or chronic wound bring about a violent cascade of cellular reactions that contributes to biological changes which further result in ongoing messenger signaling and elicits ongoing reactive cellular metabolic responses. The rapid communication between immune and body cells brings about a proliferation of specific cell types within the wound or at the wound margins and orchestrate the various stages of wound healing through photoactivation of cellular photoreceptors of large masses of cells a homeostatic intracellular metabolism and messaging. As intercellular messaging indicates homeostatic status, the reactive status of cells stabilizes through the various intracellular secondary metabolic effects and normalcy resumes among cellular function.

Further, additional surface points of irradiation may also overlay cellular structures involved in cellular energy deficits secondary to or directly resulting from involvement in auto immune and immune mediated inflammatory reactions. These include but are not restricted to arterial endothelial cells, thyroid gland cells, pancreatic cells, liver cells, intestinal mucosal cells, brain cells and meninges, nerve cells, nerve ganglia cells, spinal cord cells, muscle cells, bone cells, cartilage cells, connective tissue cells, specialized respiratory cells, fat cells, and mucosal cells. These surface areas overlying the reactive cells may be irradiated concurrently or sequentially.

When immune system cells are actively engaged in creating antigen antibody reactions they release chemical messengers. These chemical messengers create the inflammatory cascade involving many other immune system cells that res the classic immune system reaction to foreign substances. This cascade of the immune system response also involves local cell types as the inflammatory response engulfs an area. This involvement in a classical immune system reaction is in the form of energy depleting to the cells involve, while intracellular metabolism is shifted away from homeostasis toward messenger instruction mediated reactivity. Long term resolution of cascaded immune inflammatory reactions requires stopping the cascade inflammatory stimulation while addressing the energy deficit of cells already impacted by the immune messenger chemicals. Photo stimulation of cells supplies energy for resumption of normal homeostatic cell metabolism, which in turn involves the release of chemical messengers directing adjacent and distant cells toward biological equilibrium or homeostasis.

Specific immune system cellular reactions can be treated in situ at the point of immune mediated inflammation with appropriate time and dose related treatments. In addition the preferred method specifies the in situ irradiation of areas of high concentration of vascular structures containing mobile immune cells whose metabolic status may be of a reactive nature. Irradiation of vascular structures in a time related and dose specific fashion with a wavelength that is capable of penetrating to the depth of a large volume of vascular structures is best to irradiate the largest number of cells within those structures.

In reference to FIGS. 10A-11B, there may be one or plurality of hand pieces, guides, or laser devices of apparatus 100 used concurrently to irradiate acute or chronically inflamed cells in a wound as well as cells within the bloodstream moving through key vascular areas of high blood cell concentration. For example, referring to the embodiment of FIG. 10A, there can be a single source, hand piece, or guide 130 directing a laser beam having a large surface beam profile 132 for treating one or more of wound, inflammation, or autoimmune deficiency conditions in patient 30. Referring to the embodiment of FIG. 10B, there can be a plurality of laser sources such as guide 130A having beam profile 132A, laser source or guide 130B having beam profile 132B, and laser source or guide 130C having beam profile 132C, wherein each laser source, guide, or hand piece can treat various areas, parts, and treatments sites of the patient's body 40.

Figure 11A:
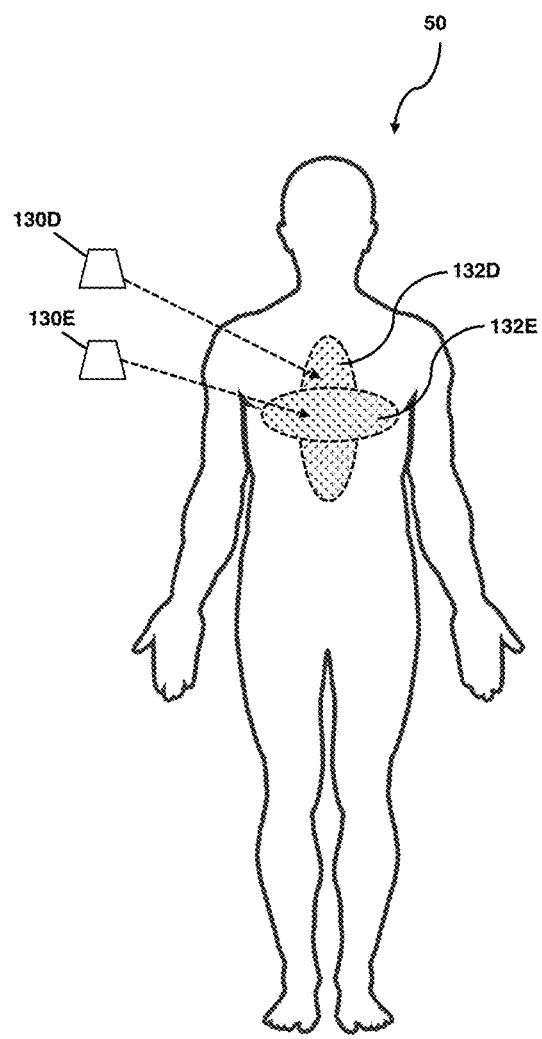
FIG. 11A illustrates another non-limiting embodiment front view diagram of a patient depicting a plurality of overlapping laser beams focused on a treatment site.
Figure 11B:
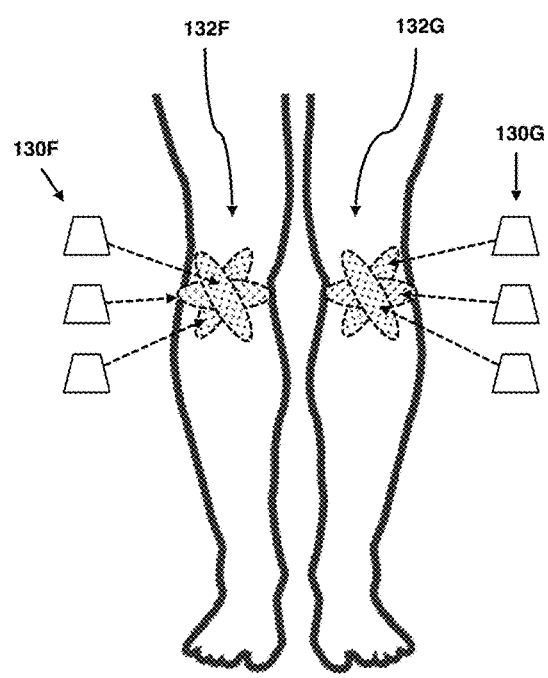
FIG. 11B illustrates another non-limiting embodiment front view diagram depicting another treatment method in which a plurality of overlapping lasers beams focused on a plurality of overlapping treatment sites.

Referring to the embodiment of FIG. 11A, there can at least two laser sources or guides 130D and 130E with their beams 132D and 132E, respectively, directed at the same treatment site area of patient 50. Here, by overlapping the projected conical distribution of laser light to coordinate with the depth of cells, the overlapping laser beams can utilize deep penetration of the 1060 nm to 1325 nm wavelengths, such as 1275 nm wavelength, and high power densities maintained below the level of cellular ablation, to increase the density of photon concentration to deep body cells. Similarly, FIG. 11B illustrates another embodiment wherein at least three laser sources 130F, collectively, are directed at one treatment site 132F and at least three laser sources 130G directed at another treatment site 132G can be utilized to further increase the photon concentrations at those sites for deeper penetration of the 1060 nm to 1325 nm wavelengths of the disclosure described herein. Further, the laser source, laser beam, or aimed optical energy can be either adjacent, in direct contact, indirect contact, near, in proximity, or at any distance with respect to the patient or treatment site.

Figure 12:
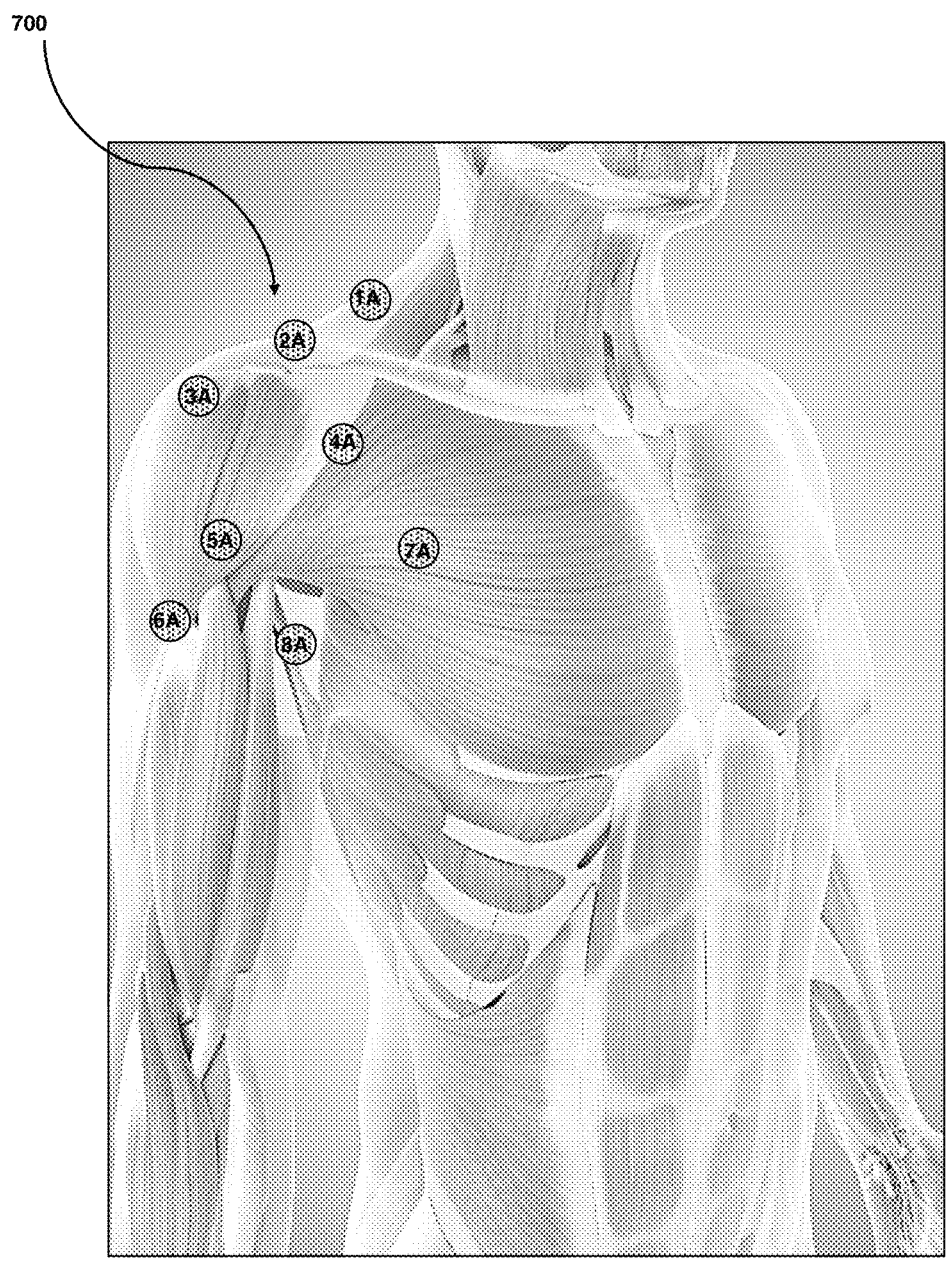
FIG. 12 illustrates one non-limiting embodiment perspective anterior view diagram of a shoulder area depicting a plurality of treatment points to be treated by the laser beam.
Figure 13:
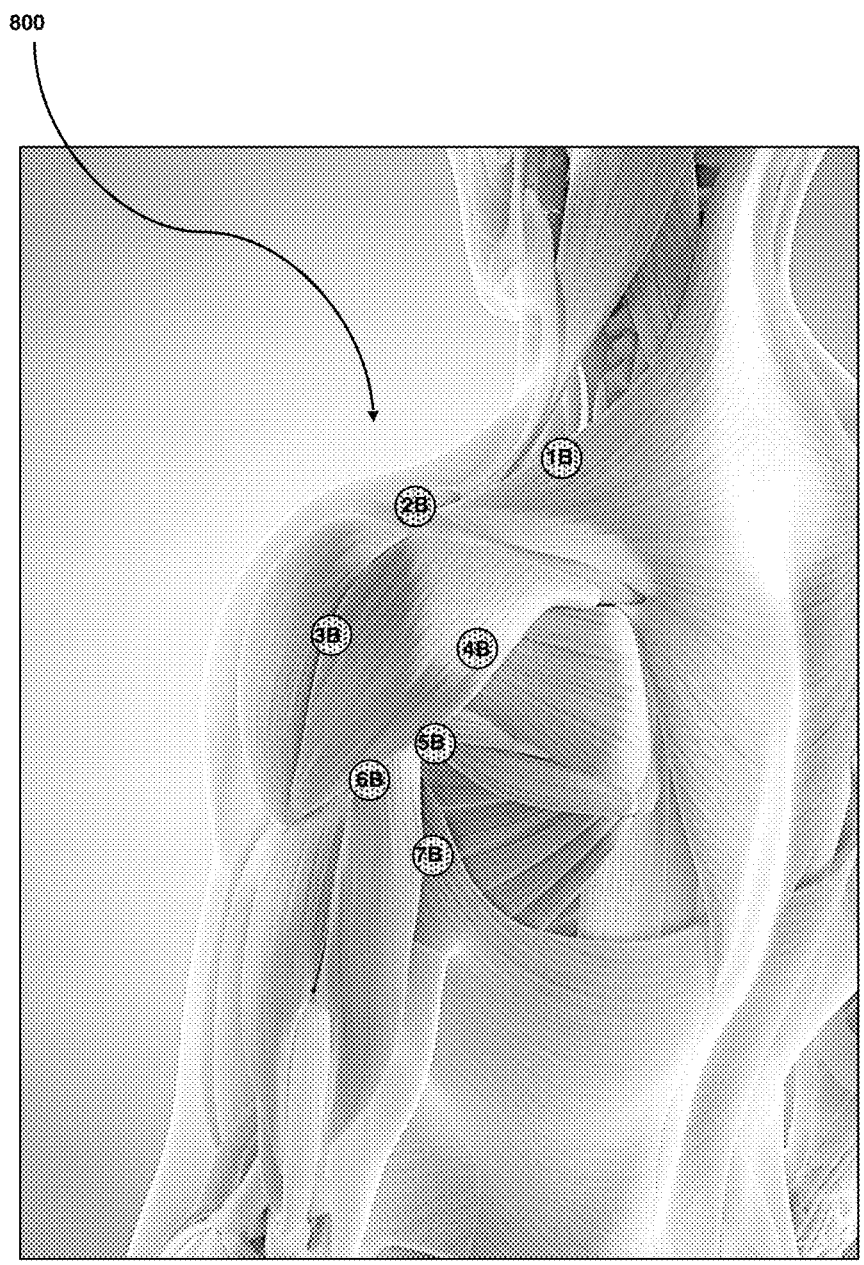
FIG. 13 illustrates another non-limiting embodiment perspective posterior view diagram of a shoulder area depicting a plurality of treatment points to be treated by the laser beam.
Figure 14:
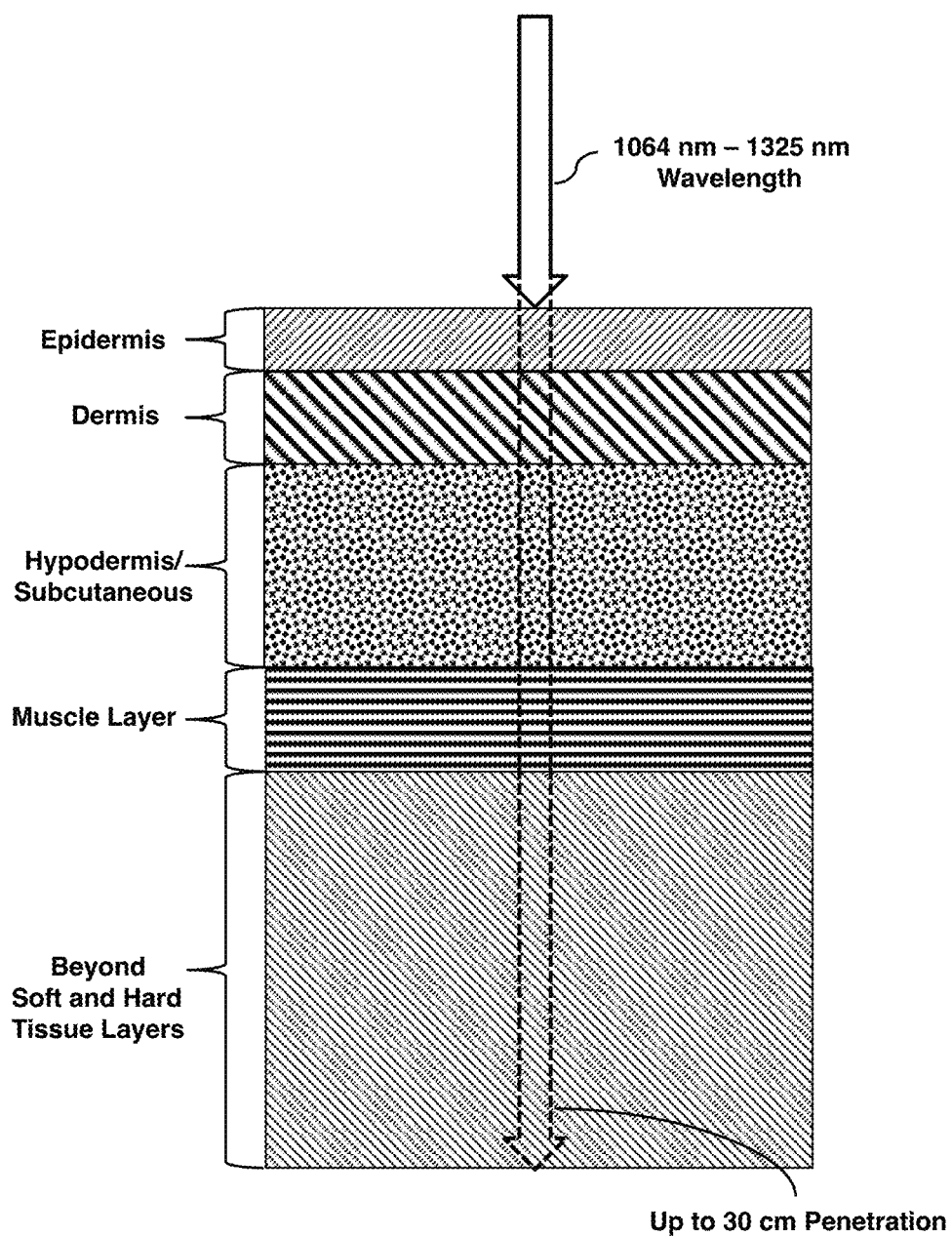
FIG. 14 illustrates a non-limiting embodiment cross-sectional view diagram of the subcutaneous tissue layers and depth of the laser beam extending beyond multiple soft and hard tissue layers.

In reference to FIGS. 12-13, an embodiment for a treatment protocol of the laser system, apparatus, and method of the disclosure described herein is provided. One embodiment for a treatment protocol of the laser apparatus 100 of the disclosure described herein can be determining the site of an injury, wound, or inflammation, establish a grid at the injury site to determine the treatment points, set the laser to an appropriate power, and treat each point for approximately 60 seconds. Referring to FIG. 12, a perspective view of an anterior shoulder area 700 is illustrated. Here, the wavelengths for the laser source or laser beam can be set to anywhere from 1064 to 1325 nm, and the power level set to 750 to 1200 mW/cm^2, wherein each treatment point 1A-8A is treated by the laser beam for approximately 60 seconds. Referring to FIG. 13, a perspective view of a posterior shoulder area 800 is illustrated. Similarly, the laser beam can be set to anywhere from 1064 nm to 1325 nm, and the power level set to 750 to 1200 mW/cm^2, wherein each treatment point 1B-7B is treated by the laser beam for approximately 60 seconds. In reference to FIG. 14, a cross-sectional view of the various layers of tissue are illustrated, wherein the wavelengths of 1064 to 1325 nm of the disclosure described herein can penetrate deep within soft and hard tissue well beyond the muscle layer, such as up to 30 cm. In addition, it is contemplated within the scope of the disclosure described herein that the penetration depth can also be controlled via a combination of one or more of the range or specified wavelengths, power levels, and beam profiles disclosed herein, among other factors.

Figure 15A:
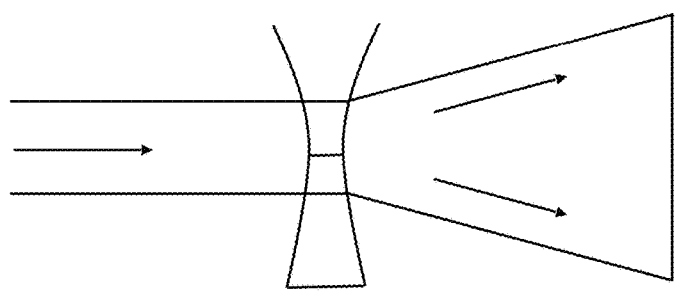
FIG. 15A-15B illustrates one non-limiting embodiment of a de-focusing lens for varying a beam profile diameter of the laser system.
Figure 15B:
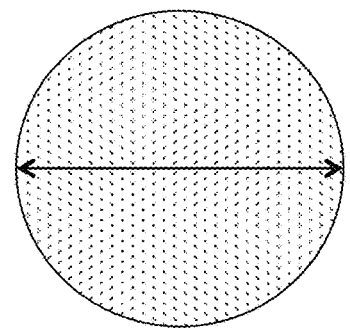
Figure 15C:
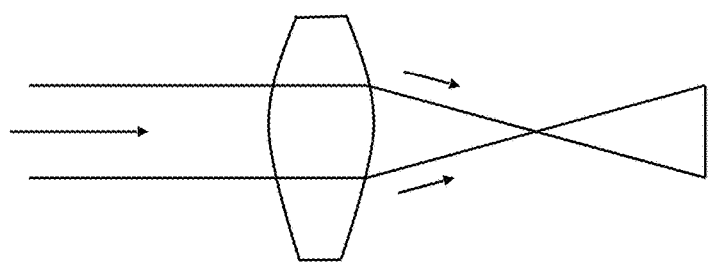
FIG. 15C-15D illustrates another non-limiting embodiment of a focusing lens for varying a beam profile diameter of the laser system.
Figure 15D:
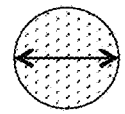
Figure 16:
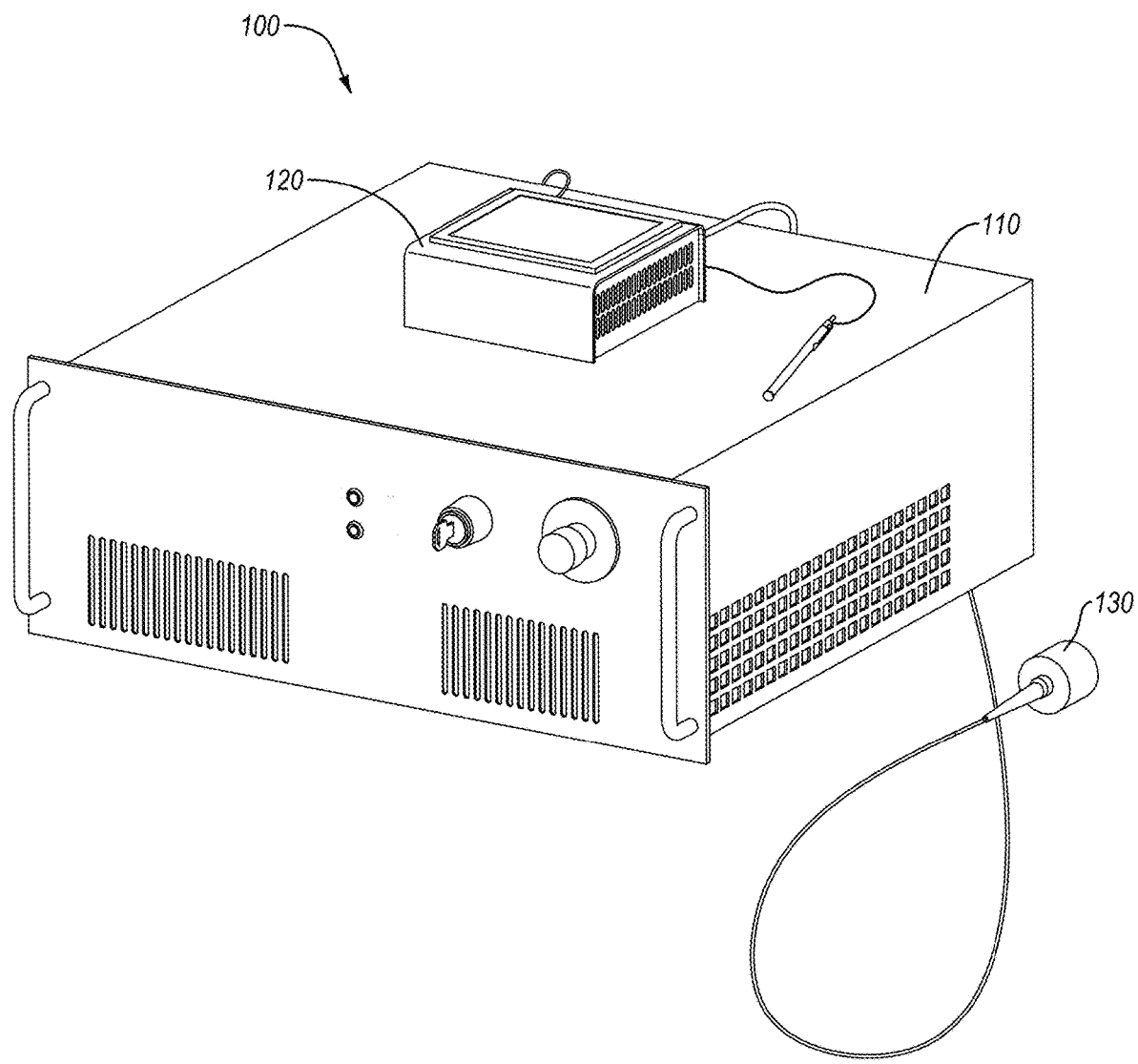
FIG. 16 illustrates another perspective view of the laser therapy apparatus of the disclosure described herein.
Figure 17A:
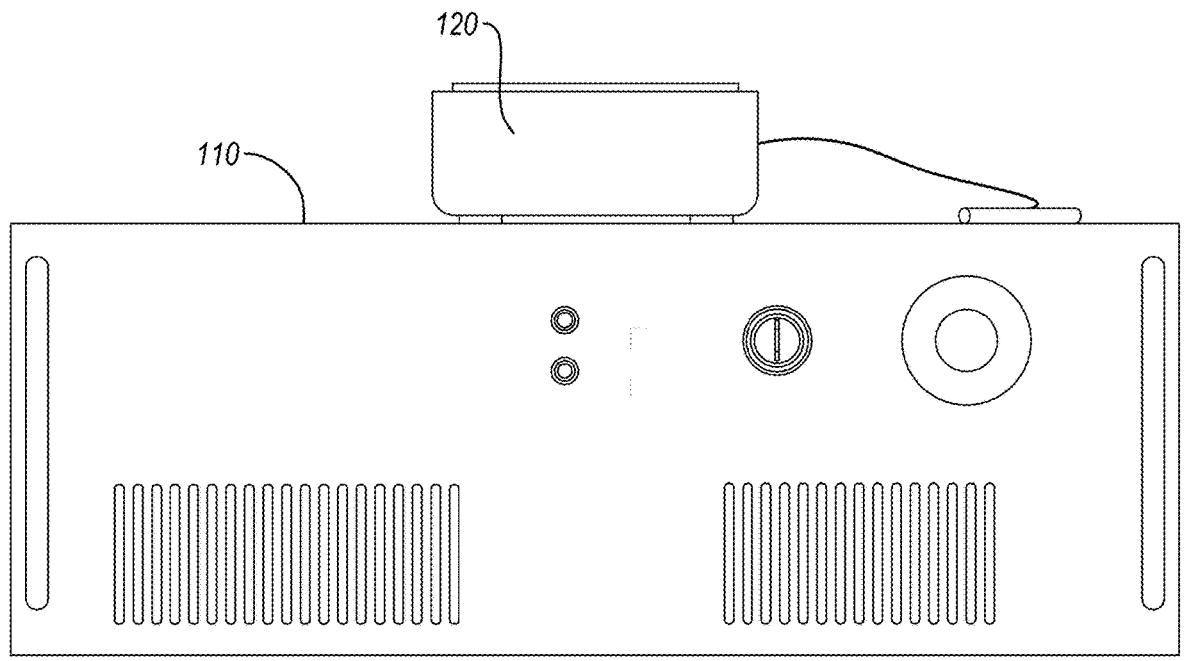
FIG. 17A illustrates a front view of the laser therapy apparatus of the disclosure described herein.
Figure 17B:
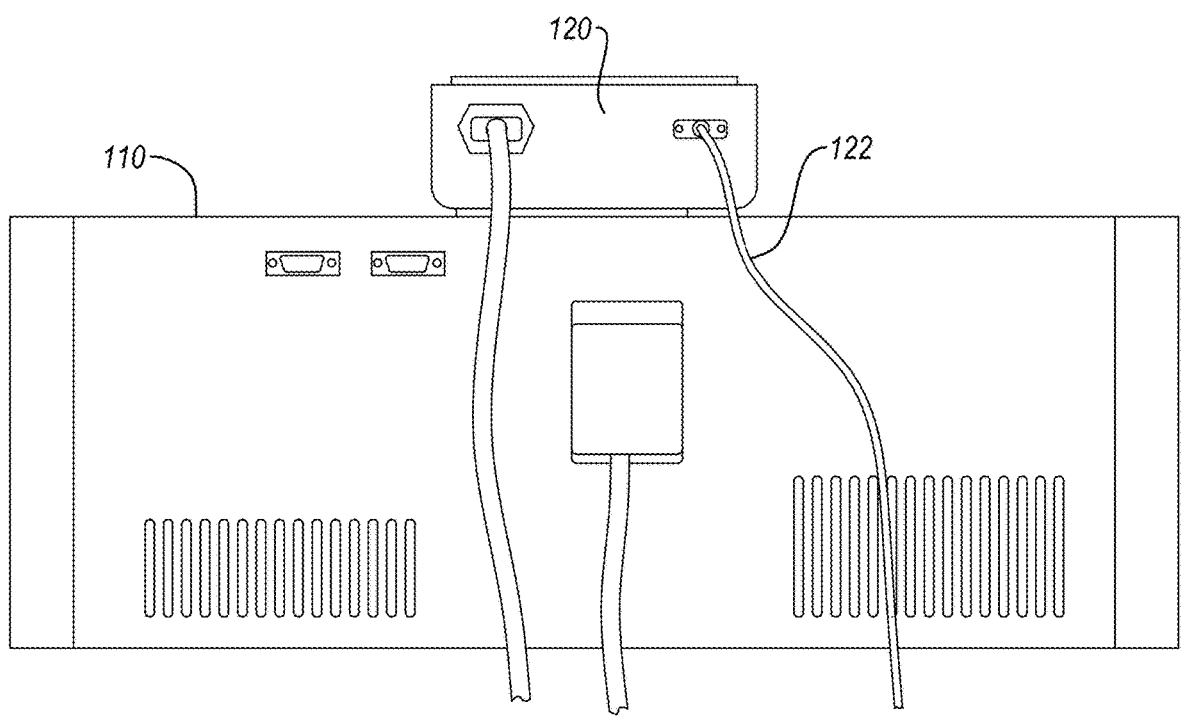
FIG. 17B illustrates a rear view of the laser therapy apparatus of the disclosure described herein.
Figure 18A:
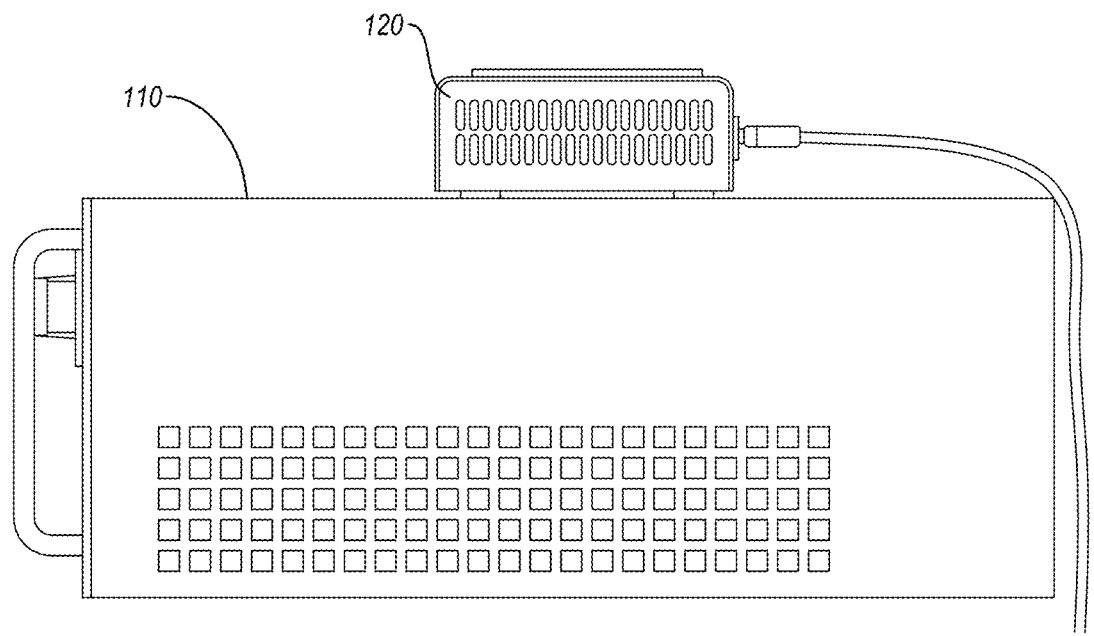
FIG. 18A illustrates a right side view of the laser therapy apparatus of the disclosure described herein.
Figure 18B:
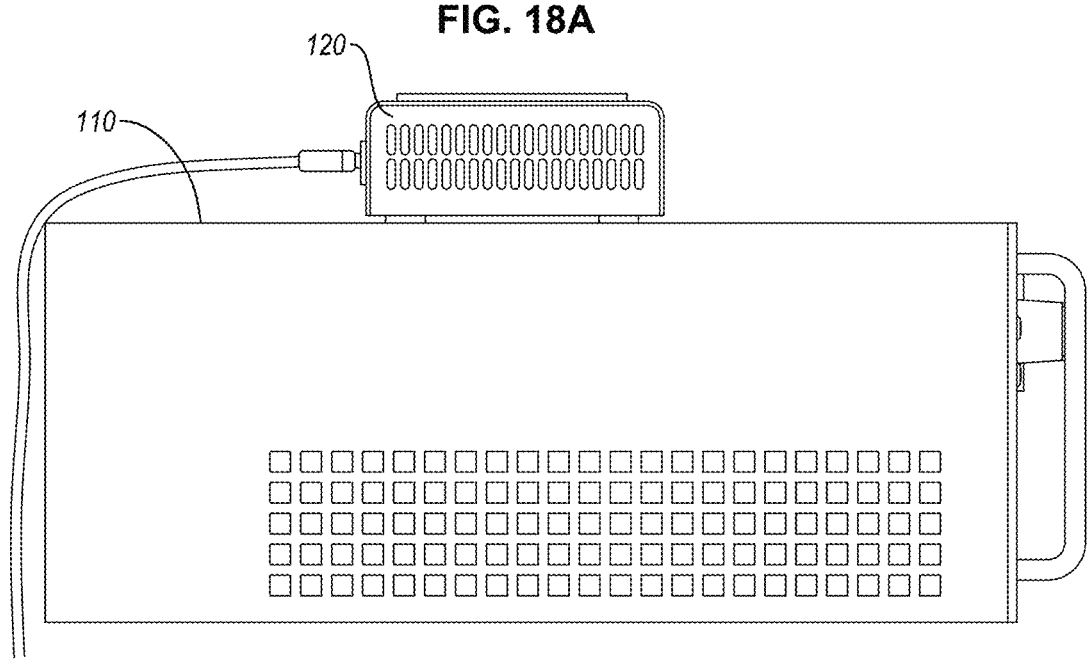
FIG. 18B illustrates a left side view of the laser therapy apparatus of the disclosure described herein.

In reference to FIGS. 15A-15D, various beam profiles can be achieved can be achieved depending on the focusing and de-focusing of the laser source. For example, FIGS. 15A and 15B illustrate one embodiment of de-focusing of the laser beam wherein a beam profile covering a large diameters can be achieved, such as from 1 mm up to 60 cm. FIGS. 15C and 15D illustrate one embodiment of focusing the laser beam to achieve smaller diameters for the beam profile. However, it is contemplated within the scope of the disclosure described herein that any type of focused or de-focused laser beam or infrared light can be used to achieve a specified beam profile diameter or beam profile surface area. Further, the beam profile surface area of the laser source or guide 130 can also be altered or modified dynamically during a treatment session or previously defined or fixed. In addition, the laser source may use any type of lens to achieve a desired beam profile, including but not limited to concave, convex, biconvex, plano-convex, plano-concave, biconcave, meniscus, and doublet, or a combination thereof. In addition, the lenses may be cylindrical, astigmatic, aspheric, achromatic, and have any type of coating. Here, the beam profile may also be modified by modifying the power output for the laser beam via the control user interface of apparatus 100. For example, a 42 W beam power output will have a larger diameter beam profile as compared to a 37 W beam power output.

The laser system, method, and apparatus of the disclosure described herein advocates the use of a homogenous or non-homogenous beam of 1060 to 1325 nm coherent laser light or optical energy beam consistent with that of the laser. The disclosure described herein claims benefits from the use of between 1060 nm and 1325 nm wavelengths of infrared light. For example, one treatment method can specifically use a pre-defined 1275 nm, and another method can vary and set the wavelengths from approximately 1150 nm to 1200 nm, another method can have a fixed or dynamically varying wavelengths from 1100 nm to 1325 nm, or from 1201 nm to 1325 nm, wherein such wavelengths can be used with laser magnitude or power levels of from 750 nm to 2.8 Watts/cm^2 range, or a power output of 1 Watt up to and including 75 W. The disclosure described herein claims deep tissue penetration from 1060 to 1325 nm wavelength laser light in accordance with established models which illustrate preferable low absorption rates in melena, hemoglobin, and water at 1060 to 1325 nm wavelengths and more specifically at 1100-1150 nm or up to 1325 nm with power levels from 750 mW/cm^2 to 2.8 Watts/cm^2 range and beam profile diameter profiles that can range from 1 inch up to 20 inches in a continuous wave, pulse wave, or repeating pattern wave. Here, the continuous wave or continuous waveform (CW) laser operation of the present disclosure described herein produces a continuous output beam, as opposed to pulsed operation. Here, the continuous wave can allow for far greater energy delivered in a shorter period of time and greater wattage and area covered by the laser allows for more coverage of surface tissue in a much shorter period of time than pulsed mode laser therapies. The CW laser operation mode can be used in conjunction with a timed duration repeat cycle, such as six (6) seconds ON and two (2) seconds OFF, and repeating this pattern for pre-defined number of times. Further, it is contemplated within the scope of the disclosure described herein that the laser may include one or more diodes and in addition to or in lieu of continuous wave (CW) operation, it may also operate in a quasi-continuous wave operation model, wherein pump source is switched on only for certain time intervals, which are short enough to reduce thermal effects significantly, but still long enough that the laser process is close to its steady state.

The disclosure described herein states that larger homogenous beam profile accompanied by higher power source results in larger total three-dimensional areas of cells in a wound to be irradiated. Cells are irradiated at powers less than that of cellular ablation. The disclosure described herein states that only through high powers, wide beam profile and specific wavelengths can the largest number of inflamed cells can be irradiated concurrently. The disclosure described herein states that concurrent irradiation of large numbers of cells initiates' photo activation of preceptors in all cells irradiated in or around the inflamed wound margins. The disclosure described herein claims that concurrent activation of photoreceptors in cells, cell metabolism moves toward physiologic equilibrium concurrently.

The disclosure described herein states that secondary cell functions occur as a result of stimulation of cellular photoreceptors and the concurrent enhancement of cellular energy status as well as the resumption of more normal cellular metabolic activity is the basis for anti-inflammatory processes initiated by specifically using either the 1275 nm or 1064 nm wavelengths and with power levels from 500 mW to 5 Watts/cm^2 range from 0.1 cm up to 60 cm, or from a power output of 1 Watt up to and including 75 Watts. The following conditions may also be treated with the optical irradiation therapy of the disclosure described herein, including but not limited to: Inflammatory arthritis, Rheumatoid arthritis, Ankylosing spondylitis, Sjogren syndrome, Osteoarthritis (degenerative joint disease), Knees, Thumb, Cervical spine, Lumbar spine, Perianritis ("frozen shoulder"), Tendonitis, Lateral epicondylitis (tennis elbow), Medial epicondylitis, Supraspinatus tendonitis, Bicipital tendinitis, Achilles tendinitis, Neuropathic pain, Carpal tunnel syndrome, Diabetic neuropathy, Radiculopathy, Radiation dermatitis, Stomatitis, Keioids, Sports injuries, Ankle sprain, Muscle pulls, Buerger's disease (Thromboangiitis Obliterans), Headaches (vascular and muscular), Pruritus, Peripheral nerve repair, Post therapeutic, Neuralgia, Orofacial pain, Dental surgery, Oral dysesthesia, Trigeminal neuralgia, Temporomandibular pain, Dental hypersensitivity, Acute and chronic musculoskeletal pain, Low back pain, Tension myalgia, Myofascial pain, Patellofemoral pain, Soft tissue wounds, Diabetic ulcers, Pressure sores, Venous stasis ulcers, Surgical Wounds, Following neurosurgery, Cranial nerve Vll (facial nerve) repair, Trigger point (elevation of pain thresholds), Sympathetic nervous system dysfunction, Hemangioma, Tinnitus immune modulation, Allergetic rhinitis, Leukemia, Bactericidal effects, and Pyronie's disease Nerve repair, among others.

Further, the types of lasers that may be used for method, system and apparatus of the disclosure herein may include, but is not limited to: Helium Neon (NeBe), Gallium aluminum arsenide (GaAlAs), Gallium arsenide (GaAs), Neodumium-yttrim-alumimum gamet (Nd: YAG), Carbon dioxide (CO2), Argon (Ar), Krypton (Kr), Ruby, and Diode, among others.

In addition, in one embodiment for a treatment action of the laser therapy system and apparatus disclosed herein can include acute inflammation reduction. More specifically, immediately after an acute injury event, the body, in response to the disruption of the integrity of vascular, soft tissue, connective tissue and neurological processes, initiates a series of biological responses. The inflammatory reaction can consist of both vascular and cellular events. Here, injury responsive components such as Mast cells, Bradykinins and Prostaglandins are activated along with the vascular responses and cellular membrane reactions. All of these combined processes and events are represented by the symptoms of edema, inflammation, pain and functional debility. Laser light therapy of the present disclosure described herein can be effective in mediating both the aforementioned symptoms and the underlying inflammatory process. Here, the laser light energy pulses of the disclosure described herein can be adjusted to penetrate more deeply and more aggressively into the skin tissue, depending on the condition and goals of treatment. The light energy, which can be delivered by either a large device that emits multiple laser panels at once, or a hand-held device for smaller targeted areas, which will pass through the skin layers to reach the cells and tissue causing the pain and inflammation. Here, the laser device can also be held against the skin over the area being treated, and the light energy is absorbed and converted to biochemical energy which stimulates the cells. The activity activates the natural healing process of the cells, which reduces pain, increases blood flow, and stimulates repair of the tissue.

In another embodiment for a treatment action of the laser therapy system and apparatus disclosed herein can include targeting inflammation. More specifically, for inflammation, the laser therapy of the disclosure described herein can cause the smaller arteries and lymph vessels of the body to increase in size, which is called vasodilatation. Vasodilatation allows inflammation, swelling, and edema to be cleared away from injury sites more effectively. Vasodilatation in lymph nodes promotes lymphatic drainage which also aids in the healing process; bruises are also often resolved faster due to this effect.

In another embodiment for a treatment action of the laser therapy system disclosed herein can include management of fibromyalgia. More specifically, the therapeutic laser light energy of the disclosure described herein has good pain relieving and anti-inflammatory effects that provide considerable pain relief for patients with fibromyalgia (FM), and can significantly increase the quality of life for such patients. The laser light therapy of the disclosure described herein combination with other treatment modalities, such as medications, can offer another positive multidisciplinary approach to FM treatment.

In another embodiment for a treatment action of the laser therapy system and apparatus disclosed herein can include back, neck, and joint pain management. In particular, there are a number of biochemical effects that have been observed with laser therapy, several of these effects relate directly to the management of the patient with chronic back pain. Three of the most prevalent features of patients suffering from chronic back pain are inflammation, pain, and edema. Further, injured cells and tissues generate enzymes that encourage the receipt of photons more readily than healthy cells and tissues do. Primary photo acceptors which are located in the mitochondria are activated by the laser light of the disclosure described herein and can convert the light energy into electrochemical energy. These are thought to be avins, cytochromes, and chromophores in the form of porphorins. Porphyrins have been shown to play an important role in the relief of low back pain. Small amounts of singlet oxygen have been shown to accumulate in tissues irradiated with laser light. Further, singlet oxygen affects the formation of adenosine-5'-triphosphate (ATP) in the mitochondria, and the red and infrared light therapy of the disclosure described herein can reduce pain by a combination of these responses. In particular, biochemical responses to the laser therapy of the disclosure described herein can include, but is not limited to: stabilization of the cell membrane, enhancement of ATP synthesis, stimulated vasodilatation along with increased histamine, nitrous oxide, and serotonin, acceleration of leukocyte activity, increased prostaglandin synthesis, reduction in interleukin-1 levels, increased angiogenesis, enhanced superoxide dismutase, and decreased C-reactive protein and neopterin levels, among others.

In another embodiment for a treatment action of the laser therapy system and apparatus disclosed herein can include neurologic response management. In particular, There are several neurologic responses to laser therapy that may influence brain recovery or prevent brain atrophy as well as several of the physiologic effects listed above. In particular, the application of laser to normal human neural progenitor (NHNP) cells can significantly increase ATP production. In addition, the laser therapy of the disclosure described herein has the potential to improve neuronal function in many patients with Parkinson's disease and other neurodegenerative diseases.

In another embodiment for a treatment action of the laser system and apparatus disclosed herein can provide deep tissue penetration and saturation. In particular, chronic low back pain is a complex clinical condition that involves many different tissue levels from subcutaneous and muscle tissues to the deeper tendons and ligaments, including the intervertebral disc. The laser therapy of the disclosure described herein is effective in treating such pain in that it will produce significant biochemical changes in the superficial, medium, and deep tissues of the treatment site. In particular, the laser light energy of the disclosure described herein can affect deep tissue structures from approximately 1 cm to 30 cm in depth.

In another embodiment for a treatment action of the laser system and apparatus disclosed herein can include wound care management. In general, laser light therapy is a form of phototherapy that involves the application of high power monochromatic and coherent light to injuries and lesions in order to stimulate wound healing. The laser light therapy apparatus of the disclosure described herein has been shown to increase the speed, quality and tensile strength of tissue repair, resolve inflammation and provide pain relief. In addition, during a laser irradiation session, cells absorb photonic energy of the laser system and apparatus disclosed herein that is incorporated into chromophores, which, in turn, stimulates cellular metabolism. Hence, the effects are photochemical, not thermal, and the responses of cells occur due to changes in photo acceptor molecules (also known as chromophores, which are molecules that are able to absorb photonic energy such as porphyrin. Here, the chromophore is able to transfer the absorbed energy to other molecules and thus cause chemical reactions in surrounding tissue. Further, the acceptor molecules' kinetic energy is increased, thereby activating or deactivating enzymes, which, in turn, are able to alter the physical and/or chemical properties of other macromolecules, such as DNA and RNA in order to facilitate wound healing. Here, the light energy which is delivered to the cells produces insignificant and minimal temperature changes, such as in the range of 0.1 to 0.5 Celsius so that the treatment is essentially painless and non-ablative of the target tissue and surrounding tissue.

Experimental Case Study for Treatment of Osteoarthritis

In another experimental case study, the laser apparatus and method of the disclosure described herein was used as a 42-Watt high intensity cold laser functioning at approximately a 1275 nm wavelength to treat osteoarthritis (OA) in former professional athletes. As compared to a low-level laser therapy (LLLT) laser having less than 1-Watt power at a wavelength of 1060 nm, the 42-Watt power and 1275 nm wavelength of the disclosure described herein helped reduce the light absorption by melanin and hemoglobin, thereby allowing the laser beam to penetrate more deeply into soft tissue. Given the beneficial effects of LLLT may be dependent on the intensity or power level of the laser device, an evaluation was performed of the high intensity laser method and apparatus of the disclosure described herein in 39 former elite NFL players with OA. The objective of this evaluation and study was to determine if high-intensity laser therapy (HILT) with the 42 watt laser therapy apparatus of the disclosure described herein could achieve a sustained reduction in joint pain at rest and with activity.

The case study included a total of 39 healthy former elite NFL football players suffering from OA from degenerative joint disease for 9±11 years, were administered 1-3 laser treatments lasting an average of approximately 10 to 20 min using an FDA-approved class IV, 42-Watt, continuous diode cold laser of the disclosure described here. In addition, the participants completed a pre-treatment questionnaire assessing the specific location and the duration of their OA joint symptoms, the severity of their pain at rest and with physical activity (using an 11-point verbal analog scale (VAS) with 0=no pain and 10=worst pain imaginable), and their current use of pain-relieving medications. The overall beneficial effect of the laser treatment(s) was assessed on an 11-point VAS with 0=no relief to 10=complete relief of their joint symptoms after their last treatment session. The VAS pain scores before and after each treatment session were analyzed using paired sample t-test, with $p<0.05$ considered statistically-significant.

Here, the mean pre-treatment (baseline) pain scores were 3.5±2.9 at rest and 6.0±2.6 with activity. Further, excluding two patients who reported no pain at rest (they were being treated primarily for 'numbness' in an extremity), the baseline pain score was 4.4±2.5 at rest. After the first laser treatment session (lasting 13±4 min), their VAS pain scores were reduced and underwent a second treatment session (lasting 10±4 min) at approximately 24 hr after the initial treatment. The baseline VAS pain score prior to the second treatment was 2.3±2.6 at rest and decreased to 0.8±1.6 ($p<0.01$) and decreased from 4.1 to 1.6±2 with activity. In the 17 former players who underwent a third treatment (lasting 10±3 min) ~24 hours after the second treatment, the VAS score decreased from 1.5±2.1 to 0.7±1.4 ($p<0.05$) at rest and from 3.5 to 1.6±2 with activity. The reduced level of pain after their last treatment session lasted one (1) to three (3) weeks in 64% of the players, and 51% of the players reported an increase in their overall level of physical activity. Only two players failed to achieve a significant reduction in their level of pain. The other beneficial effects reported on the follow-up evaluation included improved range of motion (63%), and reduced swelling (20%) and numbness (26%). Further, when asked to assess the overall improvement in their level of pain after the laser treatment(s) on a VAS scale from 0=none to 10=complete relief, the mean score was 7.2±1.8.

The results of this case study series suggest that HILT with the 42 Watt laser apparatus of the disclosure described herein, functioning at or around 1275 nm, provided a sustained reduction in joint pain due to degenerative OA in 74% of the former elite athletes after only 1-3 treatment sessions lasting 10 min to 25 min. Further, the beneficial pain-relieving effect lasted for 1-4 weeks in the majority of the former players and was not mitigated by age, weight, height, or weight-to-height ratio. In contrast to the earlier version of this cold laser technology, the laser therapy of the disclosure described herein has greater than 80 times more power and produces a greater and more sustained reduction in pain symptoms. In addition, the case study also suggests that the beneficial effects of the laser apparatus and method of the disclosure described herein is cumulative.

Experimental Case Study for Treatment of Chronic Opioid Use

In another experimental case study, a pilot study was designed to evaluate a novel nonpharmacologic approach to treating long-standing (N1 year) opioid dependency. In general, the therapy involved the use of the high intensity cold laser device (42 Watt) of the disclosure described herein operating at around 1275 nm compared to a Class III low-level laser therapy (LLLT) device operating at 0.5 Watt operating at around 635-66 nm to treat three patients who had become addicted to prescription opioid-containing analgesic medication for treating chronic (residual) pain after a major operation. After receiving a series of 8-12 treatment sessions lasting 20-40 min to the painful surgical area over a 3-4 week period of time with the high intensity (42 W) laser of the disclosure described herein, an FDA-approved Class IV cold laser, the patients were able to discontinue their use of all oral opioid-containing analgesic medications and resume their normal activities of daily living. At a follow-up evaluation 1-2 months after their last laser treatment, the patients reported that they have been able to control their pain with over-the-counter non-opioid analgesics and they have remained largely opioid-free. Further larger-scale studies are needed to verify these preliminary findings with this powerful cold laser in treating opioid-dependent patients.

In particular, with respect to a first case study involving a 32 year female subject was treated who had completed multiple orthopedic related surgical procedures following a motor vehicle accident, and who was taking Narco (hydrocodone bitartrate 10 mg and acetaminophen 325 mg) 1 tablet po QID along with ibuprofen 600 mg po TID. Her baseline pain score was 4-5 at rest and 7-8 with physical activity (using an 11-point verbal analog scale [VAS] with 0=no pain and 10=worst pain imaginable). In this case, the patient received a series of eight (8) treatment sessions lasting 30-40 min over a four week period with the laser apparatus of the disclosure described herein, an FDA-approved class IV, noninvasive, 42 W, continuous diode cold laser manufactured by Phoenix Thera-Lase, Dallas, Tex. The designated painful body areas (namely, her low back, left hip and knee) were treated with a series of 60 second treatments located approximately 3-5" apart while holding the laser hand piece 12-16" from the skin surface to avoid overheating the treatment area. At the end of the four week treatment period, her pain at rest was reduced to 2 and only increased to 3 with physical activity. Here, the subject remained free of opioids two months after completing the initial series of laser treatments.

In another study, a 44 year old female subject was treated who was experiencing chronic pain in her lumbar spine and hips after undergoing back surgery, and who was taking 2-3 Percocet (oxycodone 5 mg/acetaminophen 325 mg) tablets per day. The subject's baseline VAS pain score was 7 at rest and a 10 with physical activity. The subject received a series of 9 laser treatment sessions using the laser apparatus and method of the disclosure described herein to her low back and hip region lasting 30-40 min over a 3 week period. At the end of the 3 week period, her pain was reduced to 0 at rest and a 3 when performing her normal activities of daily living, and was considered free of opioids one month after the treatments.

Experimental Case Study for Treatment of Drug-Resistant Fibromyalgia Symptoms

In another experimental case study, the effects of the laser apparatus and method of the disclosure described herein were studied in treating drug-resistant fibromyalgia symptoms. In general, fibromyalgia syndrome (FMS) is a heterogeneous disease which can affect an estimated 12 million Americans. Further, common characteristics of fibromyalgia include widespread muscle and joint pain and fatigue, which could result in depression and anxiety. Further, there have been many pharmacological agents that have been previously used to treat the symptoms of fibromyalgia, including both opioid non-opioid analgesics. For the study, the laser apparatus and method of the disclosure described herein were studied operating at low level (1 W), intermediate level (42 W), and at a high level (75 W) HILT in a woman with fibromyalgia syndrome which had been resistant to both pharmacotherapy and treatment in an interdisciplinary pain management program.

Here, the female subject was a 67 year old having fibromyalgia for approximately 7 years and for which she had been resistant to standard pharmacotherapy. The subject's baseline pain score was 6-7 on an 11-point visual analog scale (VAS), with 0=no pain to 10=intolerable pain. The subject further completed the standard questionnaires used for assessing patients with fibromyalgia-like symptoms. In addition, her Widespread Pain Index (WPI) score was 10/18, Symptom Severity (SS) Scores were 6/9 (Part A) and 1/3 (Part B). Her symptom impact questionnaire (SIQ) score was 38.3/100, with difficulty primarily expressed for household chores, lifting and carrying groceries, climbing stairs and prolonged sitting (>45 min). Further, the subject had also completed a RAND Short Form 36 (SF-36) health survey, with scores of 45/100 on the physical functioning subscale, 0/100 on the role limitations due to physical health and emotional problem subscales, 30/100 on the energy/fatigue subscale, 56/100 on the emotional well-being subscale, 25/100 on the social functioning subscale, 10/100 on the pain subscale, and 25/100 on the general health subscale.

In addition, despite the subject receiving various types of pain management, cognitive therapy, meditation, and a limited serious of laser treatments operating 25 W at a wavelength of 810-980 nm using an alternative laser therapy apparatus and method, as well as pharmacotherapy, she reported only very minor improvement in her fibromyalgia symptoms. For the case study treatment, the laser therapy method and apparatus of the disclosure described herein (Phoenix Thera-lase System) was used, which includes a power range from 1 W to 75 W at a wavelength of 1275 nm. Initially, 42 W power at approximately 1275 nm was administered to designated body areas, such as the lower thoracic and lumbar paraspinous regions, with a series of 60 second treatment at approximately 4-6 inches apart over the symptomatic areas with a laser probe of the disclosure described herein held at approximately 12 inches from the skin surface. Here, the initial treatment was for 40 minutes and produced a beneficial result of on the subjects joint pain, namely, VAS=1-2, in addition to improved range of motion, mood, level of physical activity and quality of sleep for one-week, in which no opioid-containing analgesic medication were required. Further, during this one-week period, the subject reported a visual rating scale (VRS) score for pain relief of seven (7), wherein zero (0) is defined as no relief and ten (10) defined as complete relief.

Still referring to the study of the 67 year old female subject, after a month from the initial treatment, the subject returned for another 42 W treatment at 1275 nm lasting approximately 30 minutes for the lower thoracic and lumbar paraspinous regions. Subsequent to this second treatment, the subject reported pain relief of VRS=6 with the beneficial effect lasting for approximately four days. After two weeks following the second treatment, the subject was again administered treatment but with one (1) Watt at 1275 nm of the laser apparatus of the disclosure described herein in the same lower thoracic and lumbar paraspinous regions. After this third treatment, the subject reported minimal pain with a VRS=2-3 and lasting for 2-3 hours following the treatment. The subject further returned for another fourth treatment of the laser therapy apparatus and method of the disclosure described herein, namely, administering 75 Watts at 1275 nm of laser therapy for approximately 30 minutes to the same lower thoracic and lumbar paraspinous regions. After this fourth treatment, the subject reported a pain score of VAS=0-1 and a pain relief score of VRS=8-9, with the beneficial effect lasting for more than 10 days. After two-weeks following the fourth (75 W) treatment session, the subject fibromyalgia pain symptoms returned to greater than 50% from baseline, but was no longer using opioid-containing analgesic medications. In Here, the up to 75 W power operating at longer infrared wavelengths of approximately 1275 nm provided evidence of a sustained clinical benefit for up to 10 days after a single treatment for treatment of FMS, as compared to pharmacological therapies and less powerful and shorter wavelength laser therapy devices. More specifically, for the subject of the current study, a 42 W and 75 W treatment at around 1275 nm provided the most benefit and pain relief for 4-10 days after each treatment session, and was further able to discontinue her opioid containing medications.

Further, prior studies utilizing alternative laser therapy devices that operate at lower power levels, such as less than one (1) Watt and shorter wavelengths, such as less than 900 nm, can have an influence of light beam penetrating below the skin surface. Here, by administering a more powerful laser beam, such as from 42 W up to 75 W, with a longer wavelength, such as approximately 1275 nm, greater pain relief and for a longer duration can be achieved relative to lower power and shorter wavelength laser therapy devices.

Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the disclosure described herein is not limited to the specific forms or arrangement of parts or method of assembly described herein, except insofar as such limitations are included in the following claims. Further, it will be understood that certain features and sub-combinations are of utility and may be employed without reference to other features and sub-combinations.

What is claimed is:

1. A method of laser irradiation for alleviating the physical symptoms associated with acute or chronic inflammatory conditions comprised of:
    directing a laser beam from a high intensity laser unit in a continuous wave operation having a wavelength of about 1275 nm and a power output level of about 42 Watts on an inflamed area that is to be treated, such that the laser beam penetrates the inflamed area in a range of 0.1 cm to 30 cm; and
    activating intracellular photoreceptors via the laser beam, thereby initiating a cascade of secondary cellular metabolic effects and normalizing cellular activity towards homeostasis.

2. The method of claim 1, wherein the laser beam is directed from a laser probe positioned from approximately four (4) to six (6) inches away from the inflamed area that is to be treated.

3. The method of claim 1, wherein the laser beam is directed from a laser probe positioned from approximately 12 to 16 in. inches away from the inflamed area that is to be treated.

4. The method of claim 1, wherein a duration for a treatment session is at least approximately 30 minutes.

5. The method of claim 1, wherein the activating intracellular photoreceptors via the laser beam further generates an increase in oxygenation in or around the inflamed area margins through angionesis or revascularization, thereby providing wound healing or homeostatic cell response en masse.

6. The method of claim 5, wherein the activating intracellular photoreceptors via the laser beam further comprises stimulating production of intercellular messenger proteins and enzymes including superoxide dismutase and catalase enzymes.

7. The method of claim 1, wherein the power level is further comprised of one or more power levels ranging from 1001 mW/cm$^2$ up to and including 1200 W/cm$^2$.

8. The method of claim 1, wherein the laser beam further comprises a beam profile covering a surface area ranging from 0.1 cm$^2$ up to and including 60 cm$^2$.

9. The method of claim 1, wherein the laser beam further comprises a duration period of 60 seconds.

10. The method of claim 1, further comprising switching the laser beam from the continuous wave operation to a pulsed wave operation.

11. The method of claim 1, wherein the laser beam does not ablate cells within the inflamed treatment area or surrounding tissue area.

12. A method of laser irradiation for alleviating the physical symptoms associated with acute or chronic inflammatory conditions comprised of:
    directing a laser beam from a laser unit in a continuous wave operation having a wavelength of about 1275 nm and a power output level of about 42 Watts on an inflamed area that is to be treated.

13. The method of claim 12, wherein the laser beam is directed from a laser probe positioned from about 12 to 16 in. inches away from the inflamed area that is to be treated.

14. The method of claim 12, further comprising switching the laser beam from the continuous wave operation to a pulsed wave operation.

15. A method of laser irradiation for alleviating the physical symptoms associated with acute or chronic inflammatory conditions comprised of:
   directing a laser beam from a laser unit in a continuous wave operation having a wavelength of around 1275 nm and a power output level in a range of 37 Watts up to 75 Watts on an inflamed area that is to be treated.

16. The method of claim 15, wherein the laser beam is directed from a laser probe positioned from about 12 to 16 in. inches away from the inflamed area that is to be treated.

17. The method of claim 15, further comprising switching the laser beam from the continuous wave operation to a pulsed wave operation.

* * * * *